US010672585B2

(12) United States Patent
Robinson et al.

(10) Patent No.: US 10,672,585 B2
(45) Date of Patent: Jun. 2, 2020

(54) VACUUM PENETRATION FOR MAGNETIC ASSIST BEARING

(71) Applicant: Varex Imaging Corporation, Salt Lake City, UT (US)

(72) Inventors: Vance Scott Robinson, South Jordan, UT (US); Kasey Otho Greenland, West Jordan, UT (US); Neil Bostrom, Millcreek, UT (US); Jonathan Miller, Murray, UT (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 41 days.

(21) Appl. No.: 16/146,867

(22) Filed: Sep. 28, 2018

(65) Prior Publication Data

US 2020/0105493 A1    Apr. 2, 2020

(51) Int. Cl.
*H01J 35/10*    (2006.01)
*A61B 6/03*    (2006.01)

(52) U.S. Cl.
CPC ............ *H01J 35/103* (2013.01); *A61B 6/032* (2013.01); *H01J 2235/1013* (2013.01); *H01J 2235/1033* (2013.01); *H01J 2235/1073* (2013.01)

(58) Field of Classification Search
CPC ................... A61B 6/032; H01J 35/103; H01J 2235/1013; H01J 2235/1033; H01J 2235/1073
See application file for complete search history.

(56) References Cited

U.S. PATENT DOCUMENTS

| 4,504,965 | A | 3/1985 | Ebersberger |
| 6,198,803 | B1 | 3/2001 | Osama et al. |
| 6,327,340 | B1 | 12/2001 | Runnoe |
| 6,762,522 | B2 | 7/2004 | Steinmeyer |
| 7,203,280 | B2 | 4/2007 | Anno et al. |
| 7,206,380 | B2 | 4/2007 | Anno et al. |
| 8,385,505 | B2 | 2/2013 | Coon et al. |
| 2004/0080727 | A1 | 4/2004 | Emoto |
| 2006/0188068 | A1* | 8/2006 | Anno ................ H05G 1/04 378/130 |
| 2015/0117604 | A1 | 4/2015 | Chrost |
| 2017/0301504 | A1 | 10/2017 | Burke et al. |

* cited by examiner

*Primary Examiner* — Mark R Gaworecki
(74) *Attorney, Agent, or Firm* — Maschoff Brennan

(57) ABSTRACT

In one example, a lift assembly may exert a force on a rotatable anode of an X-ray source. The lift assembly may include a lift shaft and a lift electromagnet. The lift shaft may be coupled to an anode and configured to rotate around an axis of rotation of the anode. The lift electromagnet may be configured to apply a magnetic force to the lift shaft in a radial direction. The lift electromagnet may include a coupling portion extending between an interior of a vacuum envelope and an exterior of the vacuum envelope and a winding portion coupled to the coupling portion. Windings may at least partially surround the winding portion.

20 Claims, 21 Drawing Sheets

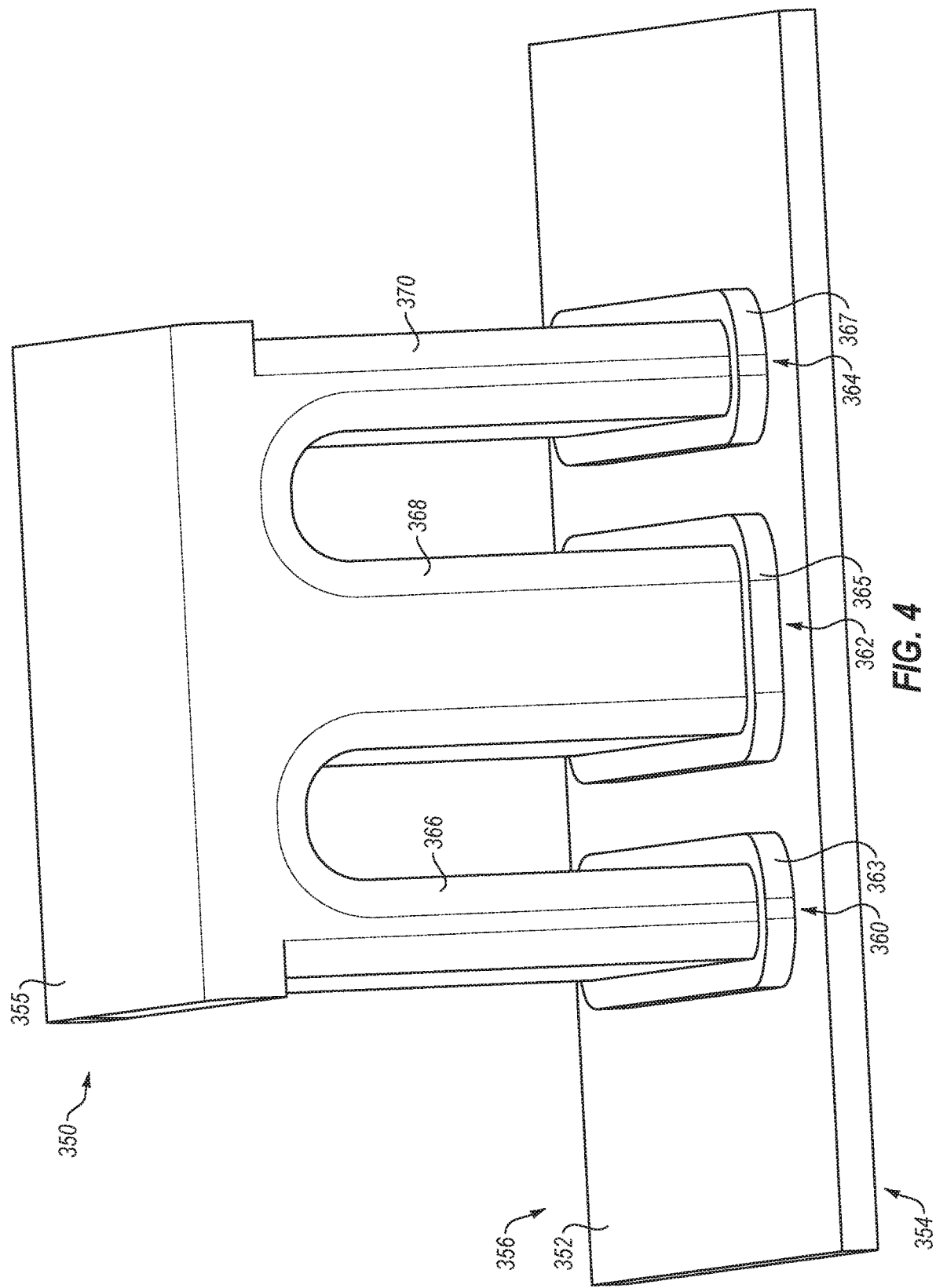

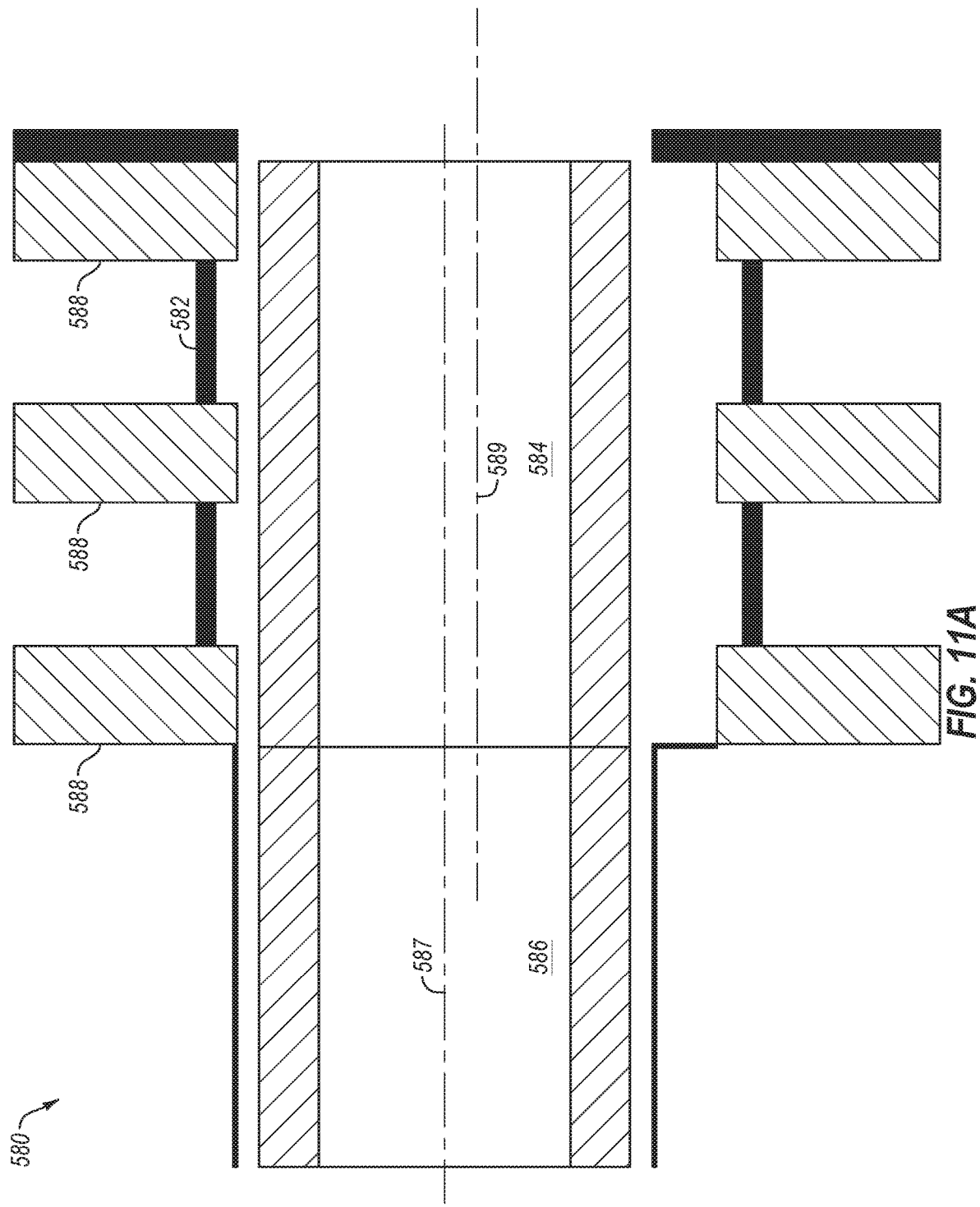

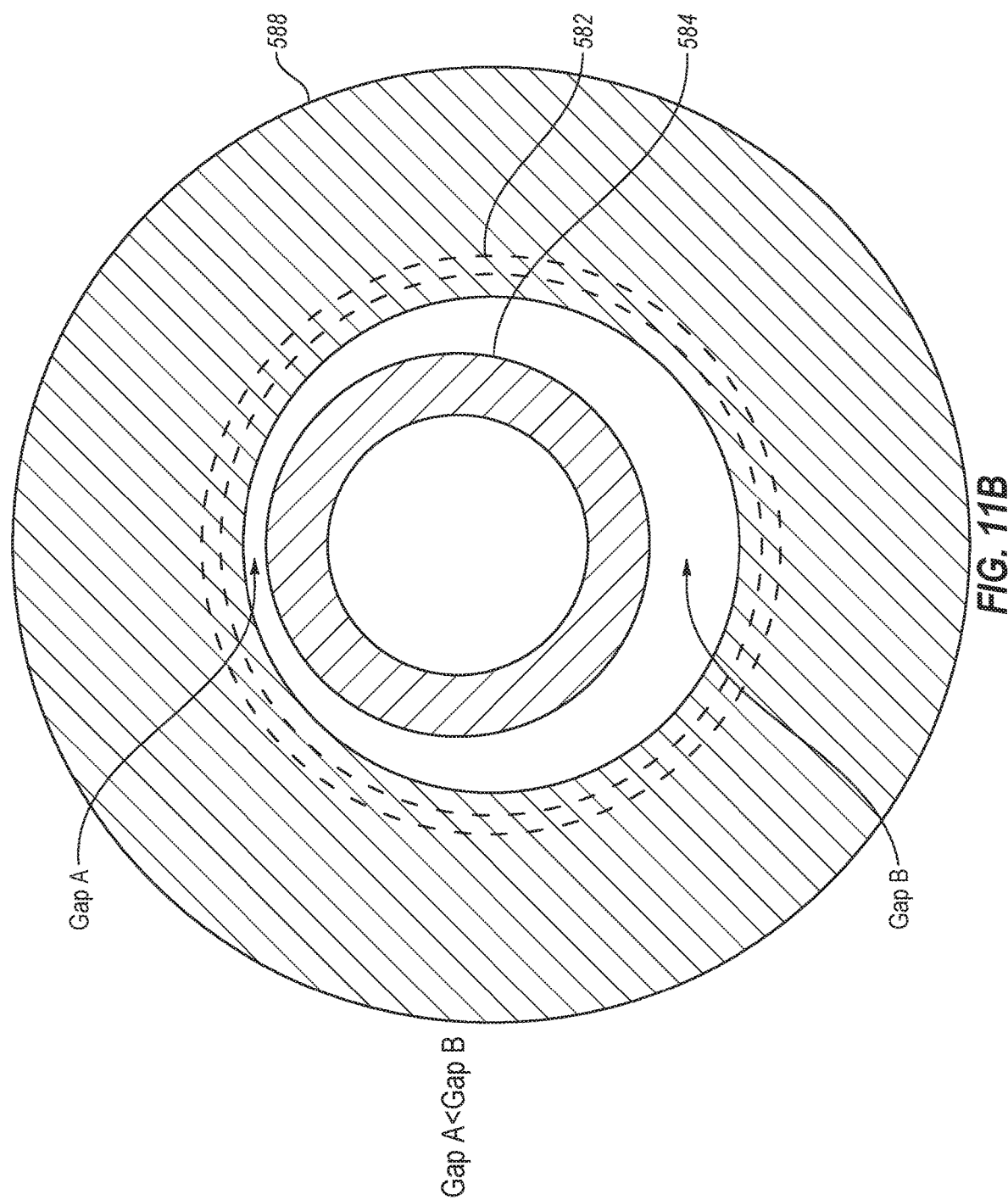

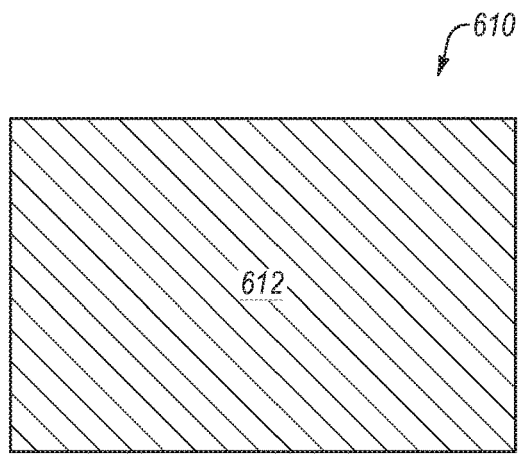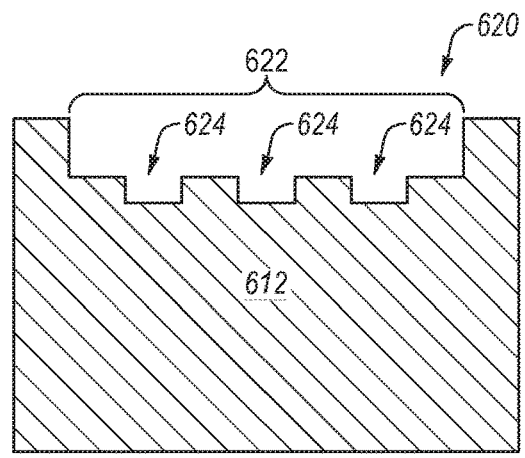
FIG. 12A   FIG. 12B
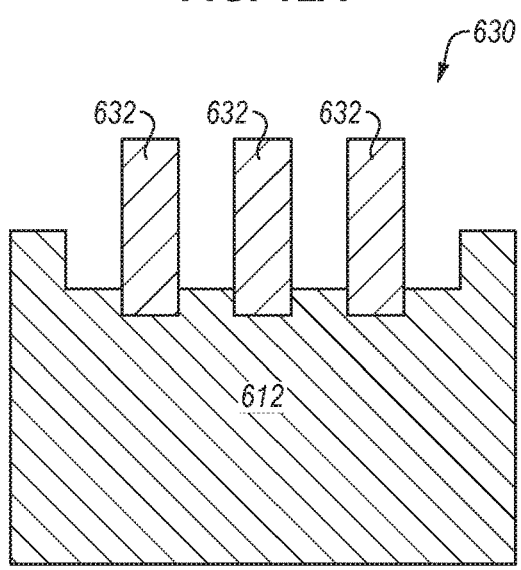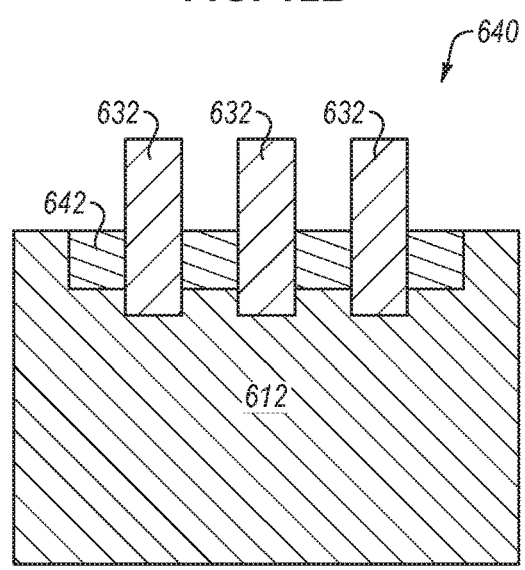
FIG. 12C   FIG. 12D
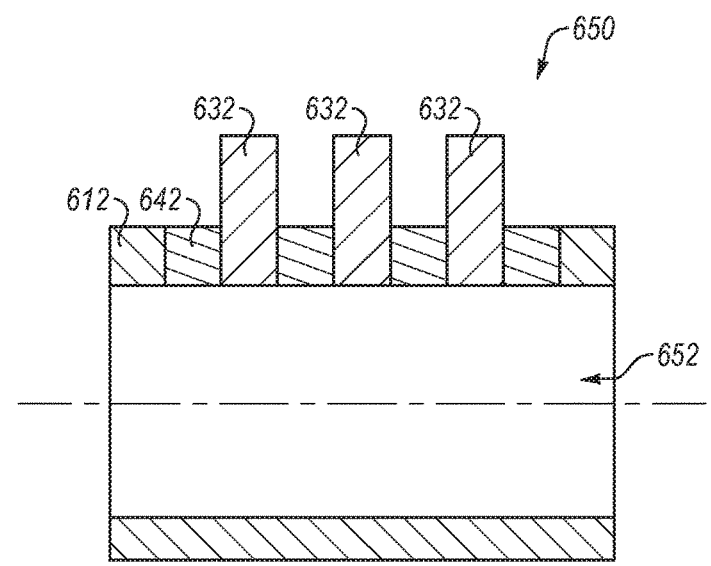
FIG. 12E

US 10,672,585 B2

VACUUM PENETRATION FOR MAGNETIC ASSIST BEARING

BACKGROUND

The present disclosure generally relates to X-ray imaging systems, including embodiments relating to magnetic lift assemblies for X-ray sources used in X-ray imaging systems.

X-ray imaging systems typically include an X-ray source, a detector, and a support structure, such as a gantry, for the X-ray source and the detector. In operation, the X-ray source typically emits radiation, such as X-rays, toward an object. The radiation passes through the object and impinges on the detector. The detector receives the radiation and transmits data representative of the received radiation.

The X-ray source includes a cathode and an anode separated by a vacuum gap. X-rays are produced by applying an electrical current to an emitter of the cathode which emits electrons. The electrons accelerate towards and then impinge upon the anode. When the electrons impinge on the anode, some of the energy is converted to X-rays. The majority of the energy in the incident electron beam converts to heat in the anode. Because of high temperatures generated when the electron beam strikes the target, the anode can include features to distribute the heat generated, such as rotating a disc-shaped anode target. The disc-shaped anode target may be rotated by an induction motor via a bearing assembly.

The X-ray source and radiation detector can be components in an X-ray imaging system, such as a computed tomography (CT) system or scanner, which includes a gantry that rotates both the X-ray source and the detector to generate various images of the object at different angles. The gravitational (G) forces imposed by the rotation of the gantry and/or the rotation of the anode may result in stresses on components of the X-ray source. In particular, G forces resulting from the rotation of the gantry and/or the anode may result in stress on the bearing assembly of X-ray sources with rotating anodes. In addition, the stress on the bearing assembly may increase as rotation speeds increase, but increased rotation speeds may be desirable for high-performance X-ray sources and CT systems. The present disclosure includes solutions related to reducing the stresses on bearing assemblies in rotating X-ray imaging systems (e.g., CT scanners).

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

FIG. 4 illustrates a perspective view of an example of a lift electromagnet that may be implemented in an X-ray source.

FIGS. 11A-11B illustrate cross section views of another example embodiment of a lift electromagnet.

FIG. 12A-12E illustrates a schematic cross sectional representation of example manufacturing steps for a lift electromagnet.

DETAILED DESCRIPTION

Reference will be made to the drawings and specific language will be used to describe various aspects of the disclosure. Using the drawings and description in this manner should not be construed as limiting its scope. Additional aspects may be apparent in light of the disclosure, including the claims, or may be learned by practice.

The invention relates to reducing the loading on a bearing assembly of an anode assembly of an X-ray source using magnetics and, more particularly, to an electromagnet for lifting a shaft of the anode assembly to counter balance forces on the bearing assembly in a computed tomography (CT) system. The electromagnet may counter balance forces on the bearing assembly due to gantry rotation, anode rotation, gravity, etc. Example embodiments include a lift electromagnet (or magnetic actuator or lift magnet) in various positions relative to the anode and bearing assembly and various variations of the lift electromagnet and component to support magnetic lift on the bearing assembly in the anode assembly. In some circumstances, the magnetic lift may also be referred to as a magnetic assist bearing.

Reference will now be made to the drawings to describe various aspects of example embodiments of the disclosure. It is to be understood that the drawings are diagrammatic and schematic representations of such example embodiments, and are not limiting of the disclosure, nor are they necessarily drawn to scale.

Figure 1:
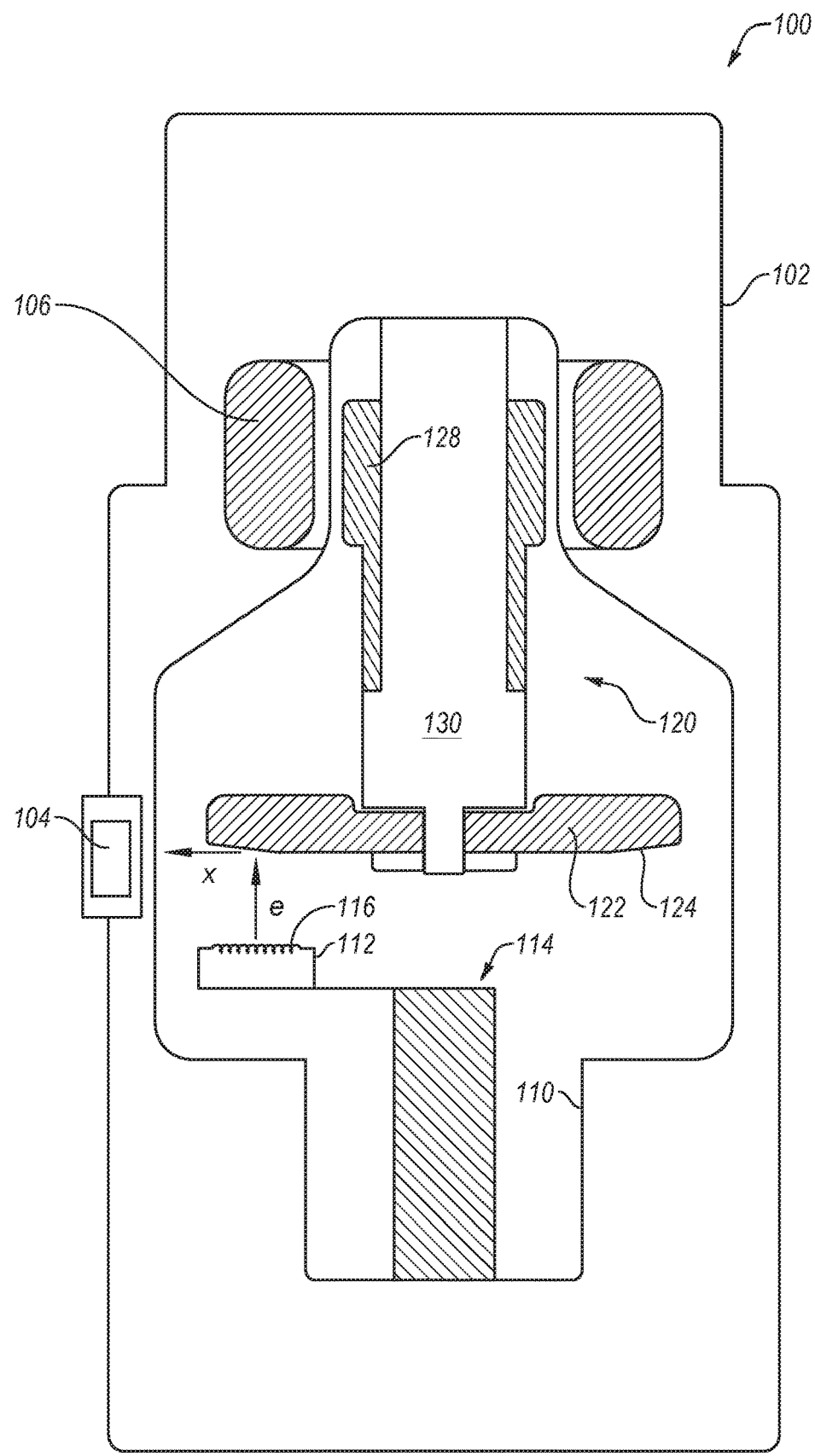
FIG. 1 illustrates a schematic diagram of an example X-ray source.

FIG. 1 is a schematic diagram of an example rotary or rotating anode X-ray source 100 with a rotatable disc-shaped anode 122. The X-ray source 100 includes a housing 102 and an X-ray insert 110 within the housing 102. The housing 102 encloses the insert 110. A fluid coolant such as a dielectric oil or air may fill the space or cavity between the housing 102 and the insert 110 to dissipate heat generated by the X-ray source 100.

A cathode 112 and an anode assembly 120 are positioned within an evacuated enclosure (or vacuum envelope) defined by the insert 110. The anode assembly 120 includes the anode 122, a bearing assembly 130, and a rotor 128 mechanically coupled to the bearing assembly 130. The anode 122 is spaced apart from and oppositely disposed to the cathode 112. The anode 122 and cathode 112 are connected in an electrical circuit that allows for the application of a high voltage difference (or high electric potential) between the anode 122 and the cathode 112. The cathode 112 includes an electron emitter 116 that is connected to a power source.

Prior to operation of the X-ray source 100, the insert 110 may be evacuated to create a vacuum, which may be enclosed by the insert 110. During operation, heat and electrical potential is applied to the electron emitter 116 of the cathode 112 to cause electrons, denoted as "e" in FIG. 1, to be emitted from the cathode 112 by thermionic emission. The application of a high voltage differential between the anode 122 and the cathode 112 then causes the electrons "e" to accelerate from the electron emitter 116 toward a focal spot on a focal track 124 that is positioned on the anode 122. The focal track 124 may include, for example, a material having a high atomic ("high Z") number such as tungsten (W), rhenium (Re) or other suitable material. As the electrons "e" accelerate, they gain a substantial amount of kinetic energy, and upon striking the rotating focal track 124 some of this kinetic energy is converted into X-rays, denoted as "x" in FIG. 1.

The focal track 124 is oriented so that emitted X-rays "x" may travel through an X-ray source window 104. The window 104 includes an X-ray transmissive material, such as beryllium (Be), so the X-rays "x" emitted from the focal track 124 pass through the window 104 in order to strike an intended object and then a detector to produce an X-ray image.

As the electrons "e" strike the focal track 124, a significant amount of the kinetic energy of the electrons "e" results in heat, a large portion of which is transferred to the focal track 124, particularly in the region of the focal spot. To reduce the heat at a specific focal spot on the focal track 124, a disc-shaped anode target is rotated at high speeds, typically using an induction motor that includes a rotor 128 and a stator 106. The induction motor can be an alternating current (AC) electric motor in which the electric current in the rotor 128 needed to produce torque is obtained by electromagnetic coupling with the stator winding. The rotor 128 is mechanically coupled to the anode 122 through a hub of the bearing assembly 130 such that rotation of the rotor is transferred to the anode. In other configurations, the motor can be a direct current (DC) motor.

To avoid overheating the anode 122 from the heat generated by electrons "e", the rotor 128 rotates the anode 122 at a high rate of speed (e.g., 80-300 Hz) about a centerline of a shaft so that the region of the anode exposed to the beam of electrons "e" varies along the focal track 124. The X-ray source 100 can also include other cooling features to manage the heat generated by the anode 122 and the cathode 112.

An X-ray source (such as the X-ray source 100) and a radiation detector can be included in a rotational X-ray imaging system, such as a computed tomography (CT) scanner. CT involves the imaging of the internal structure of an object by collecting several projection images ("radiographic projections") in a single scan operation ("scan"), and is widely used in the medical field to view the internal structure of selected portions of the human body. Typically, several two-dimensional projections are made of the object, and a three-dimensional representation of the object is constructed from the projections using various tomographic reconstruction methods. From the three-dimensional image, conventional CT slices through the object can be generated. The two-dimensional projections are typically created by transmitting radiation from an X-ray source through the object and collecting the radiation onto a two-dimensional imaging device (i.e., radiation detector), or imager, which may include an array of pixel detectors (simply called "pixels"). One example of such a CT system is shown in FIG. 2A.

Figure 2A:
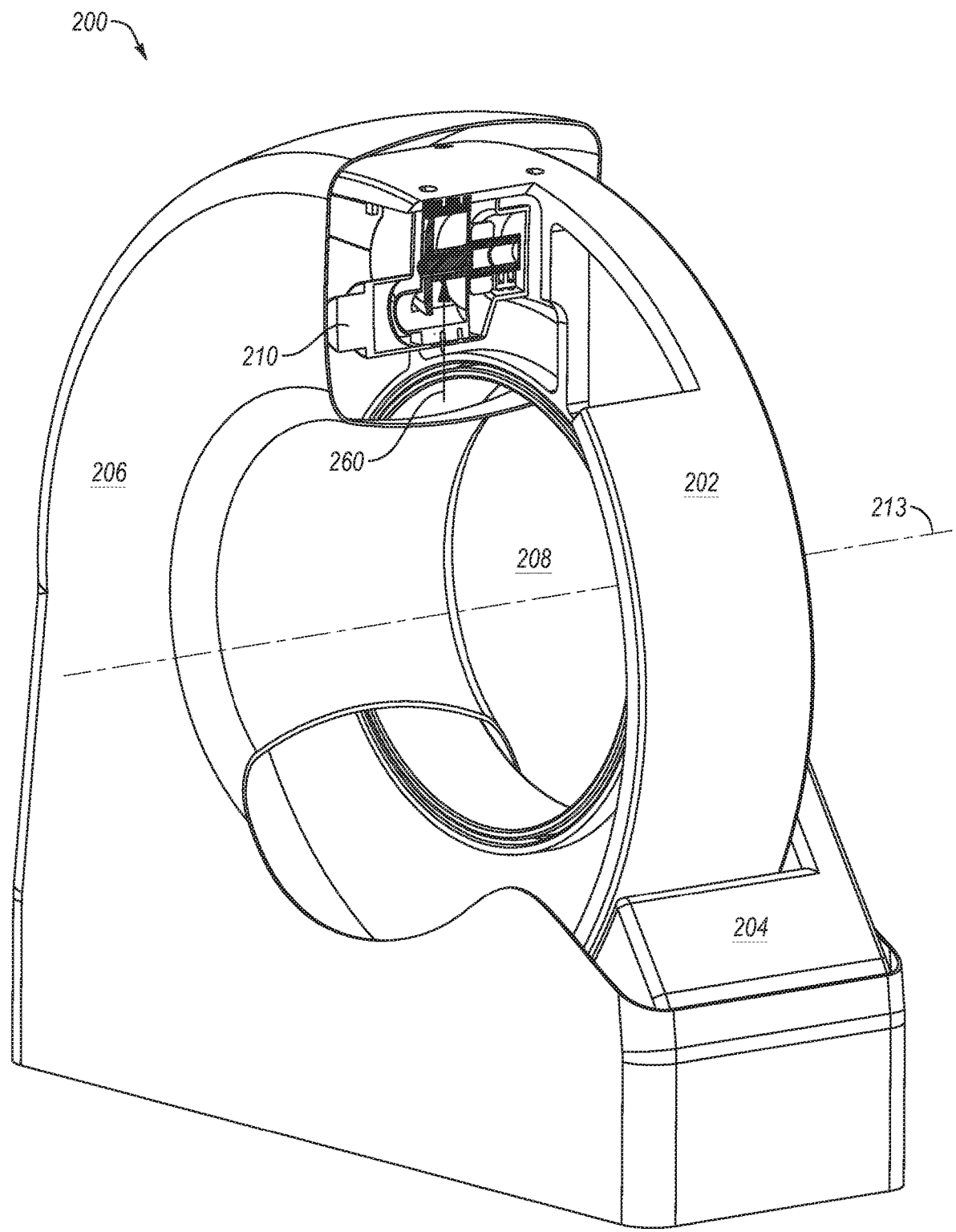
FIG. 2A illustrates a perspective view of an example gantry.

FIG. 2A illustrates an example of a gantry 200 of a rotating X-ray system. In some circumstances the gantry 200 may be referred to as a rotating assembly or a gantry assembly. The gantry 200 includes a stationary gantry frame 204 that supports a rotatable gantry frame 202. The rotatable gantry frame 202 may support an X-ray source 210 and a radiation detector or imager (not shown). The gantry 200 also includes a gantry cover 206 to enclose the rotating components and/or the stationary gantry frame 204 as well as provide an aesthetic covering.

The rotatable gantry frame 202 may include an annular shape (i.e., ring shape) that rotates about a center of axis in a gantry aperture 208 of the rotatable gantry frame 202. The centrifugal force (or gantry force), denoted via arrow 260, on components disposed on the rotatable gantry frame 202 may exceed a unit of gravitational force (g-force, G's, g's, or G loads), and may be a multiple of the g-force (e.g., 20 times the g-force). For example, components on the X-ray source 210, such as the bearing assembly, may experience a force of 37 g's if the X-ray source 210 is mounted on the rotatable gantry frame 202 at a radius of 0.7 meters from the center of axis and the rotatable gantry frame 202 is rotating at 0.275 seconds/rotation (sec/rot).

Generally, it is desirable for CT scanners to operate at higher rotational gantry speeds. However, operating CT scanners with gantries that rotate at higher speeds may adversely affect X-ray source bearing life because the bearing assemblies experience larger forces (e.g., g-forces from gantry rotation). In such circumstances, higher gantry speeds, and resultant centrifugal forces 260, can decrease the life of the bearing assembly.

Some X-ray sources implement liquid metal bearings (LMB), which may be capable of effectively handling higher forces (e.g., g-forces). However, implementing LMB can significantly increase costs and may require significant changes to the system design (e.g., the design of the X-ray source).

Other X-ray sources may implement magnetic lift configurations to magnetically assist in supporting the rotating components of the X-ray source and to decrease the forces on the bearing assembly. In some circumstances, such configurations may be advantageous over LMB because they may be implemented in existing imaging systems and/or they may provide very cost effective backwardly compatible improvements. With attention to FIG. 2B, an example of a magnetic lift configuration will be described in further detail.

Figure 2B:
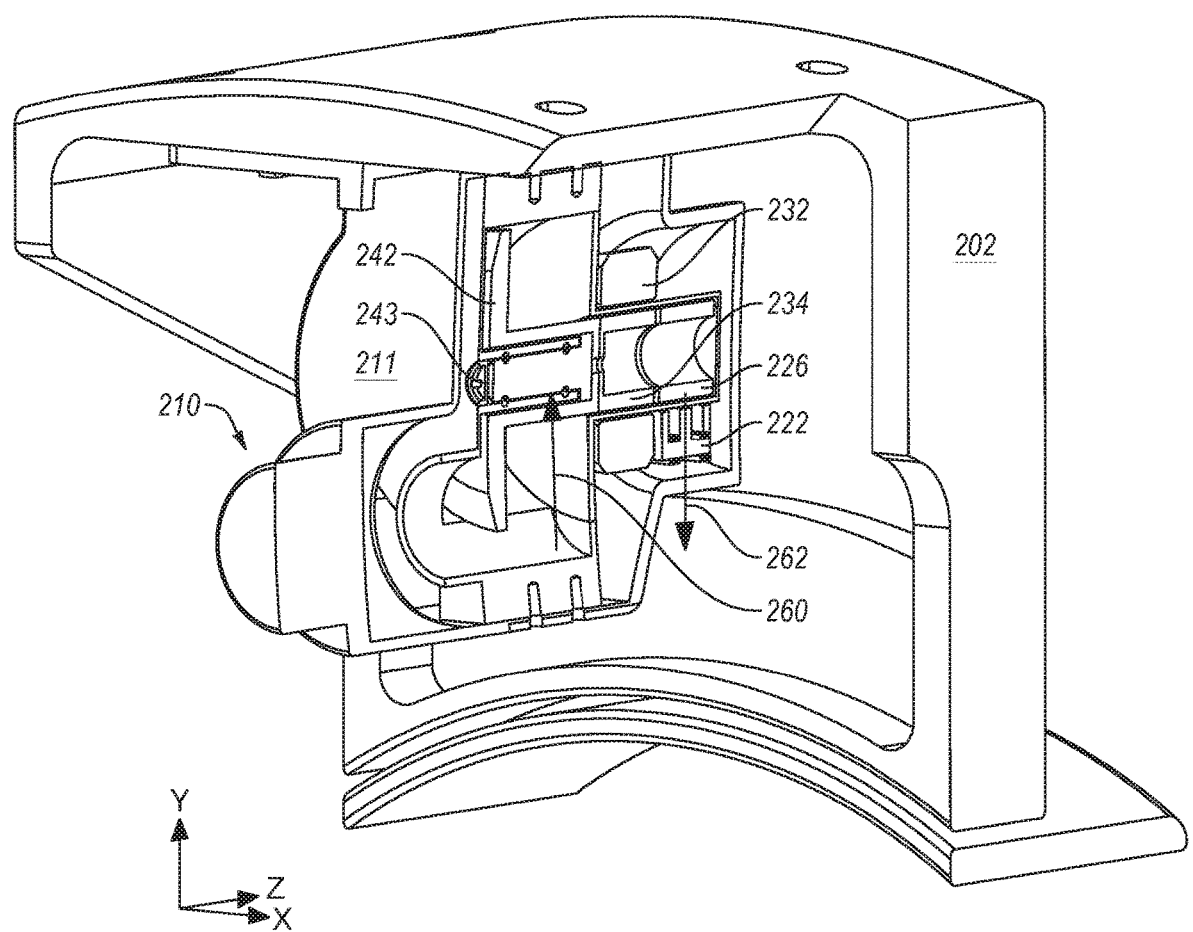
FIG. 2B illustrates a perspective view of a portion of the gantry of FIG. 2A that includes a rotating anode X-ray source.

FIG. 2B illustrates a portion of the gantry 200, and in particular, the X-ray source 210 attached to the rotatable gantry frame 202. The X-ray source 210 includes a source housing 211, an anode 242 that can receive electrons emitted by a cathode (112 of FIG. 1), a rotor 234 coupled to a shaft 243 of the anode 242, a stator 232 surrounding the rotor 234, a ferromagnetic lift shaft 226 coupled to the rotor 234, and a lift electromagnet 222 (or lift multipole electromagnet or electromagnet) that can provide a magnetic lift force, denoted via arrow 262, to the lift shaft 226 and thereby "lift" the rotor 234 and the shaft 243 of the anode 242 along the radial direction with respect to the axis of rotation of the gantry in opposition to the centrifugal force.

As used herein, lifting refers to an application of force along the radial direction of the lift shaft 226. The lifting or lift force can be an attractive force that pulls two components together (e.g., the lift shaft 226 and the lift electromagnet 222) or a repulsive or repelling force that pushes two components apart (e.g., the lift shaft 226 and the lift electromagnet 222). In this disclosure, reference will be made to the lifting or the lift force as an attractive force, but the lifting or the lift force can be a force with any magnitude (positive or negative) along the radial direction.

For descriptive purposes, FIG. 2B includes a Cartesian coordinate system with the y-axis in the vertical direction, the x-axis in the horizontal direction, and the z-axis orthogonal to the x-y plane. The rotation of the gantry 200 occurs in the x-y plane and the centerline of the shaft 243 of the anode 242 or the axis of rotation of the anode 242 extends parallel to the z-axis. During gantry rotation, a centrifugal force 260 is applied to the X-ray source 210 orthogonal-axis 213 of the gantry 200.

The lift electromagnet 222 may apply the magnetic lift force 262 (e.g., magnetic force, counter acting force, or balancing force) in substantially the opposite direction of the centrifugal force 260 so as to offset, dampen, reduce, or balance the forces (including the centrifugal force 260 of the gantry 200) on the bearing assembly or anode assembly. The magnetic lift force 262 may result in one or more of the following: reduce vibration or noise, increase bearing life, increase the bearing load capability, control thermal contact, improve the centering and precision of the rotating assembly, and allow the use of smaller bearings (e.g., ball bearings or other rotating bearings). Additionally or alternatively, the assistance of the magnetic lift force 262 may permit the use of other bearing types in a rotating anode X-ray source. In the case of medical imaging, reducing vibration and noise may also improve the patient's and/or medical staff's experience.

Figure 3A:
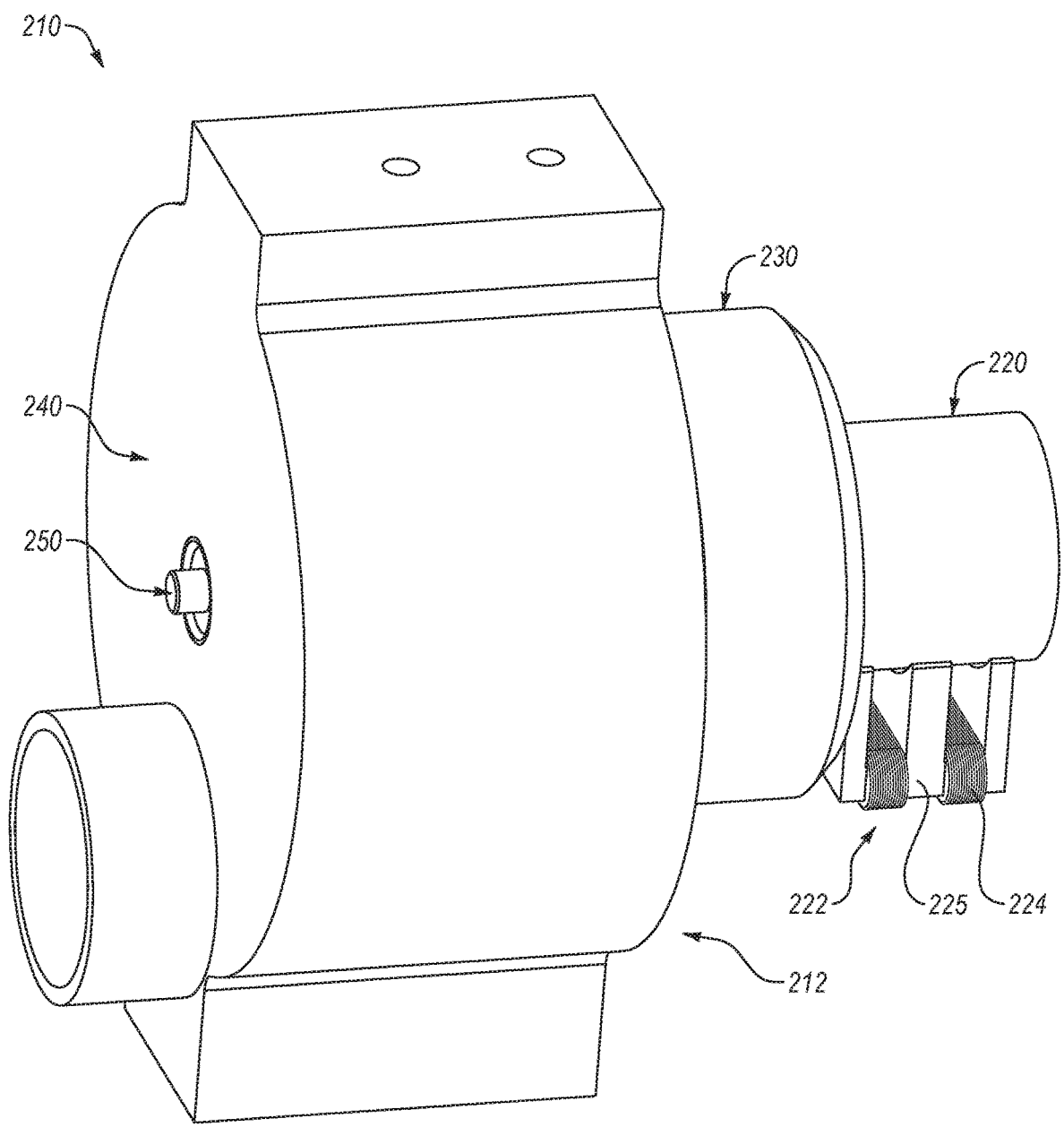
FIG. 3A illustrates a perspective view of another example of an X-ray source.

FIG. 3A illustrates a perspective view of the X-ray source 210. As shown in FIG. 3A, the X-ray source 210 may include an envelope, also referred to as an insert, 212 that includes a wall (e.g., insert wall, vacuum wall or vacuum envelope wall) that encloses the cathode and anode in an evacuated enclosure (or vacuum envelope). The insert 212 may enclose an anode assembly 240, a bearing assembly 250, a motor assembly 230 and a lift assembly 220. The lift electromagnet 222 may include a lift electromagnet core 225 with three poles formed in an "M" or "W" shape with windings (or coils or wires) 224 wrapped around the core 225 between the poles as shown, or around the poles.

Figure 3B:
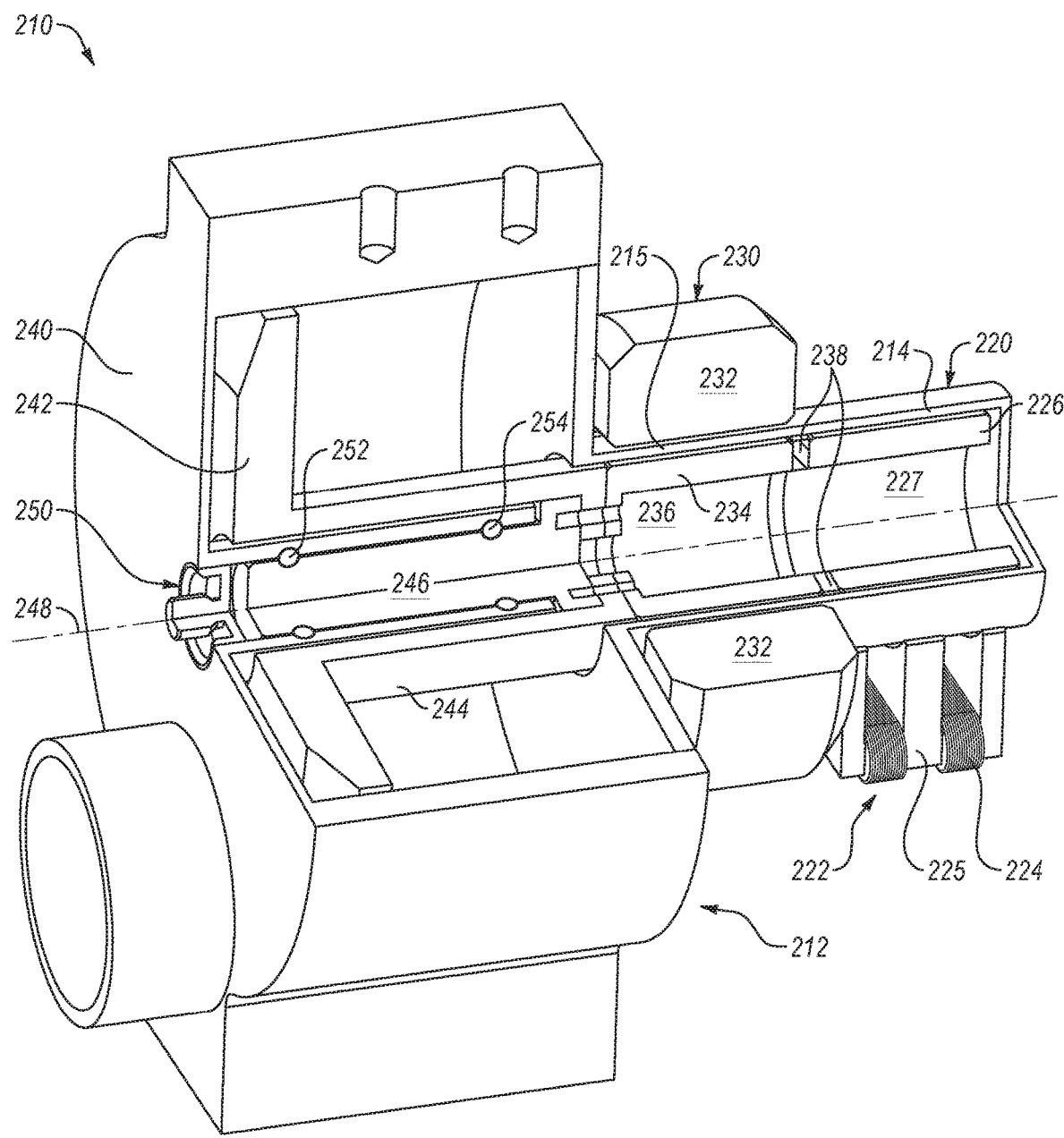
FIG. 3B illustrates a perspective section view of the X-ray source of FIG. 3A.
Figure 3C:
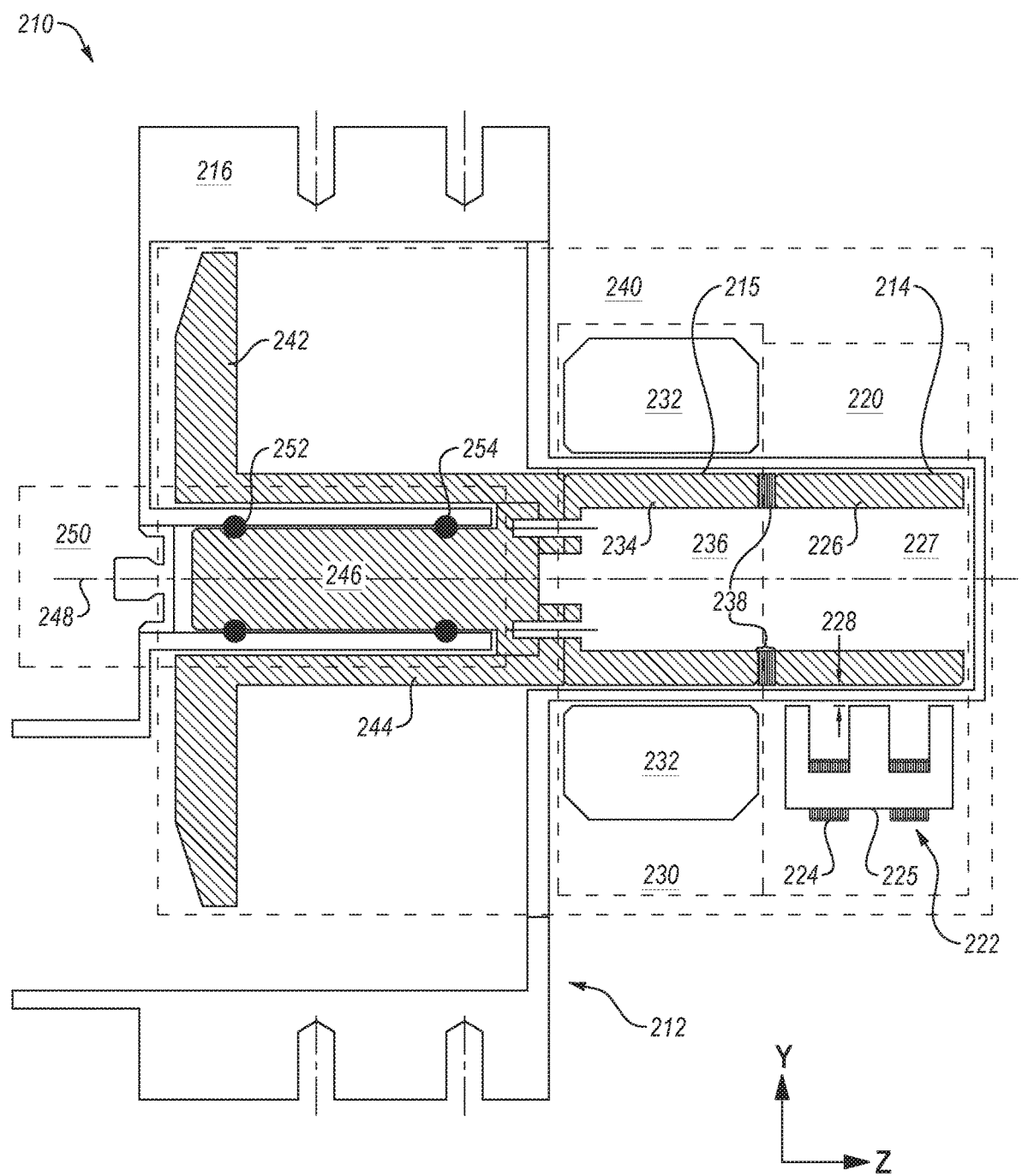
FIG. 3C illustrates a side cross section view of the X-ray source of FIG. 3A.

FIG. 3B illustrates a perspective section view of the X-ray source 210 and FIG. 3C illustrates a side cross section view of the X-ray source 210. As shown in FIGS. 3B-3C, the anode assembly 240, the bearing assembly 250, the motor assembly 230, and lift assembly 220 may facilitate rotation about an anode assembly centerline (or bearing centerline) 248. The anode assembly 240 includes an anode 242 and an anode outer shaft 244 that supports the anode 242. The anode assembly 240 also includes an anode inner shaft 246 that is coupled to the anode outer shaft 244 and rotatably coupled to the bearings 252 and 254 of the bearing assembly 250.

The anode inner shaft 246 may include at least one bearing race (e.g., ball bearing race). For example, in the illustrated configuration the bearing assembly 250 includes the outer ball bearing 252 and a corresponding race on the anode inner shaft 246, and an inner ball bearing 254 and a corresponding race. As used herein, outer refers to a relative position closer to an edge of the anode assembly 240, closer to the anode 242, or further away from the motor assembly 230. Inner refers to a position closer to a middle of the anode assembly 240, further away from the anode 242, or closer to the motor assembly 230.

Although the illustrated embodiment includes a roller element bearing (e.g., tool steel ball bearing or tool steel raceways), in other embodiments other bearing types may be implemented. For example, other configurations may include plain bearings (e.g., a sleeve bearing or a journal bearing), or hydrodynamic bearings, such as liquid metal bearings. U.S. patent application Ser. No. 14/968,078, filed Dec. 14, 2015, entitled, "Antiwetting Coating for Liquid Metal," which is hereby incorporated by reference in its entirety, discloses an example of a liquid metal bearing.

The motor assembly 230 may include a stator 232 and a rotor 234. The rotor 234 includes a rotor void 236 or opening on one end, which may be cylindrical. The rotor void 236 allows the rotor 234 to be attached to the anode shaft (e.g., the anode inner shaft 246) and/or aligned with the bearing centerline 248. The components (e.g., the anode shaft, the rotor 234, or the rotor shaft) may be attached to each other using a permanent or semi-permanent fastening or attachment mechanisms. An insert wall 215 (or a portion of the insert wall) proximate the motor assembly 230 may be disposed between the rotor 234 and the stator 232. The electromagnetic induction from the magnetic field of winding of the stator 232 may pass through the insert wall 215 to the rotor 234. A small gap between the insert wall 215 and the rotor 234 allows the rotor 234 to rotate without mechanical resistance.

The lift assembly 220 includes the lift shaft 226 coupled to the rotor 234 and the lift electromagnet 222 that may apply a magnetic force on the lift shaft 226. The lift shaft 226 may include a lift shaft void 227 or an opening, which may be cylindrical. A rotor-to-lift shaft adapter 238 may couple the rotor 234 to the lift shaft 226. The rotor-to-lift shaft adapter 238 can include a non-ferromagnetic material to improve magnetic isolation between the motor assembly 230 and the lift assembly 220 which both use magnetic fields for operation. In non-illustrated configurations, the lift shaft 226 may be integrated with or permanently attached (e.g., welded or brazed) to the rotor 234.

The lift electromagnet 222 may include at least two poles that are oriented towards the lift shaft 226. In some configurations, the lift electromagnet 222 may include three poles (tri-pole) formed in an "M" or "W" shape with windings 224 wrapped around the core 225 (or a core web) between the poles.

Material choices may affect the performance of a magnetic device, such as the lift electromagnet 222 or the lift shaft 226. Magnetic material needs to stay magnetized in vacuum (e.g., the vacuum envelope of an X-ray source) and after processing and be vacuum compatible, such as cold drawn carbon magnetic iron (CMI-C).

The lift electromagnet 222 or the lift shaft 226 may include ferromagnetic and/or ferrimagnetic materials. As used herein and for simplicity in describing the technology, a "ferromagnetic" material refers to a material that can exhibit spontaneous magnetization (i.e., either a ferromagnetic material or a ferrimagnetic material).

The windings 224 around the core 225 may include an electrical conductive material (e.g., copper or aluminum) with an electrically insulated sheath, such as enameled magnet wire (i.e., transformer wire or Litz wire).

Two factors that can reduce the lift force between the lift shaft 226 and the lift electromagnet 222 are the size of the lift gap and the presence of interstitial materials such as the insert wall with magnetic permeability greater than 1. As shown in FIG. 3C, a lift gap 228 may be the spacing between the lift shaft 226 and the lift electromagnet 222. The lift gap 228 may include the insert wall 214 proximate the lift assembly 220 along with a vacuum between the insert wall 214 and the lift shaft 226. In some examples, the lift gap 228 may include the space between the insert wall 214 and the lift electromagnet 222 when the lift electromagnet 222 does not touch the insert wall 214, such as when the lift electromagnet 222 and the insert wall 214 have different electrical potentials. The lift gap 228 that includes the vacuum provides clearance for the lift shaft 226 to rotate without mechanical resistance (e.g., friction from touching the insert wall 214 or the lift electromagnet 222).

Vacuum and air have a relative magnetic permeability (represented by $\mu_r$), of 1, thus they don't dampen the electromagnetic coupling between the electromagnet shaft 226 and the lift electromagnet 222. The insert wall 214 is typically made of a conductive material with a magnetic permeability >1 such that it can dampen the electromagnetic coupling between the lift electromagnet 222 and the lift shaft 226 reducing the lift force.

Magnetic permeability is the measure of a material's ability to support the formation of a magnetic field within itself. Relative magnetic permeability is the ratio of the magnetic permeability of a given material to that of free space. Reducing the thickness of the insert wall 214 and/or using materials with low relative magnetic permeability will ensure that damping of the magnetic force generated between the lift electromagnetic 222 and the electromagnet shaft 226 is minimized. The insert wall 214 in the lift region may include materials with a low magnetic permeability or minimal ferromagnetic properties, such as stainless steel. Additionally, reducing the lift gap 228 may increase the magnetic force applied to the lift shaft 226 by the lift electromagnet 222. The force of the lift electromagnet 222 on the lift shaft 226 is inversely proportional to the square of the lift gap, which force F can be approximated at low fields by the simplified formula $F=1/gap^2$, where the lift gap 228 is represented by gap. In one example, the lift gap 228 may be less than 2 millimeters (mm). In another example, the lift gap 228 may be less than 1 mm.

For the magnetic flux of the magnetic field to primarily act on the lift shaft 226 instead of between poles, the distance between pole ends may be at least ten times greater than the lift gap 228. In an example, the insert wall 214 in the lift region may be less than 1 mm.

The lift assembly 220 may apply a magnetic lift force on the rotating assembly (via the lift shaft 226), which can, for example, improve the operating lifespan and/or increase the load bearing capability of the bearing assembly 250 and components thereof. The magnetic force of the lift electromagnet 222 may be used to counteract loads on the bearing assembly 250, such as the centrifugal force of the gantry (e.g., the gantry 200), as well as to dampen vibration and add stability to the anode assembly (e.g. anode assembly 240) or other rotating components of the X-ray source. The forces generated by the lift assembly 220 may be applied anywhere on the rotating assembly including at the center of mass (or not at the center of mass) and may employ one or a combination of magnetic lift devices that provide the forces.

The X-ray source 210 may include any suitable features described in U.S. patent application Ser. No. 15/464,142, filed Mar. 20, 2017, entitled, "Magnetic Lift Device for an X-Ray Tube," which is incorporated herein by reference in its entirety. In particular, the X-ray source 210 may include any suitable aspects of the lift assemblies described in the above-referenced application, or any other suitable features.

As mentioned, reducing the lift gap 228 may increase the magnetic force applied to the lift shaft 226 by the lift electromagnet 222. Accordingly, in some embodiments it may be desirable to decrease the lift gap 228 in order to increase the magnetic force exerted on the lift shaft 226 by the lift electromagnet 222. Additionally or alternatively, the lift gap 228 may be decreased so a smaller or less powerful lift electromagnet may be implemented in the lift assembly 220.

Figure 3D:
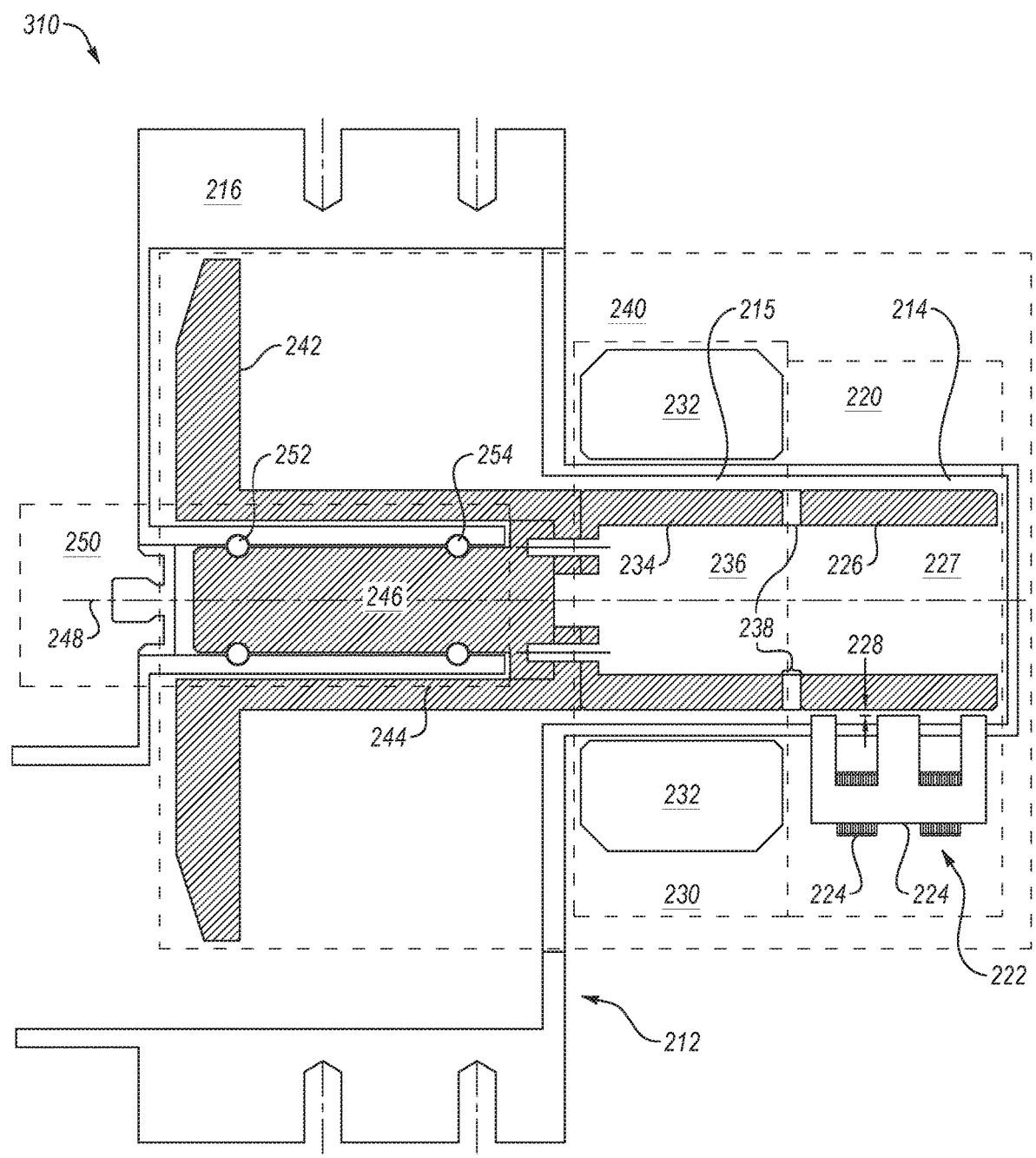
FIG. 3D illustrates a side cross section view of another example of an X-ray source.

FIG. 3D illustrates a side cross section view of another example of an X-ray source 310. The X-ray source 310 may include any suitable features described above with respect to the X-ray source 210, and similar features are indicated with the similar numbering. However, in the configuration of FIG. 3D, the X-ray source 310 includes a lift assembly 320 with a lift electromagnet 322 that is integrated into an insert wall 314. Specifically, the poles of the lift electromagnet 322 are integrated into the insert wall 314, which reduces the size of a lift gap 328 relative to, for example, the lift gap 228 of FIG. 3C, and thereby increases the strength of the magnetic field exerted on the lift shaft 226 by the lift electromagnet 322.

In configurations where the poles of the lift electromagnet 322 are integrated into insert wall 314, the insert wall 314 may not contribute to the lift gap 228, which leads to a reduction of the lift gap 228, for example, by approximately 1 mm (e.g., a thickness of the insert wall 314). Such configurations may require higher precision in components of the lift assembly 220, such as the lift shaft 226, the lift electromagnet 222, and/or the insert wall 214.

Integrating the lift electromagnet 322 into the insert wall 314 may pose various challenges. For example, the poles of the lift electromagnet 322 extend through the insert wall 314 to the interior of the vacuum enclosure and therefore must be coupled to the insert wall 314 in a manner that does not compromise or decrease the ability of the vacuum enclosure to be evacuated. Accordingly, the joint between the insert wall 314 and the poles of the lift electromagnet 322 must be hermetic so the vacuum inside of the insert wall 314 is not compromised. In addition, the joint must be compatible with downstream manufacturing processes for the X-ray source 310, which may involve high temperatures and other strenuous conditions. Furthermore, the joint must be formed while maintaining high dimensional accuracy for both the joint and other components of the X-ray source 310. In some circumstances, the required dimensional accuracy may be within +/−0.05 mm In another example, the vacuum wall (e.g., the insert wall 314) surrounding the poles of the lift electromagnet 322 or the electromagnet penetration must be configured in a manner to minimize any damping of the magnetic field created by the lift electromagnet 322. In yet another example, the materials used for the lift electromagnet 322 on the interior of the vacuum must be vacuum compatible (e.g., does not contaminate the evacuated enclosure and/or does not decrease the integrity of the vacuum) and must maintain the desired magnetic properties. Furthermore, such materials must maintain vacuum compatibility and desired magnetic properties during the operating conditions of the X-ray source 310, which may involve relatively high temperature and large forces.

Accordingly, the disclosed embodiments include configurations to integrate the poles of the lift electromagnet 322 into the insert wall 314 to reduce the size of the lift gap 328 and thereby increase the strength of the magnetic field exerted on the lift shaft 226 by the lift electromagnet 322. Such configurations may include plugs, patches, or inserts secured to the insert wall, for example, by brazing or welding, to embed the poles in the insert wall. The disclosed configurations do not compromise or decrease the ability of the vacuum enclosure to be evacuated and the joint attaching the plugs, patches, or inserts may be hermetic so the vacuum envelope is not compromised. In addition, the disclosed configurations are compatible with existing manufacturing processes for X-ray sources, and may be formed while maintaining high dimensional accuracy for both the joint and other components of X-ray sources. Furthermore, the materials used for the plugs, patches, or inserts on the interior of the vacuum may be vacuum compatible and may maintain desired magnetic properties. For example, the materials may be low carbon steel, high purity iron, cobalt-iron, nickel-iron, or other suitable materials.

The lift electromagnet 322 includes the windings 324 wrapped around a core 325 between the poles or around the poles themselves (not shown). The windings 324 may generally be formed of an electrical conductive material (e.g., copper or aluminum) with an electrically insulated sheath, such as enameled magnet wire (i.e., transformer wire). However, the material of the windings 324 (e.g., the conductive material or the electrically insulated sheath) may have relatively low heat tolerance, and thus may not be able to tolerate high temperature manufacturing steps of the X-ray source, such as annealing, welding or brazing. In addition, the poles or the core 325 of the lift electromagnet 322 may include ferromagnetic and ferrimagnetic materials, which may lose their magnetic properties if they exceed the Curie temperature for that material. However, the high temperature manufacturing steps of the X-ray source (e.g., brazing) may exceed the Curie temperature, which may cause the material to lose its magnetic properties without a slow cooling process after a high temperature operation or a re-annealing process. Thus, it may be desirable for certain portions of the lift electromagnet 322 not to exceed high temperatures during manufacturing.

Accordingly, some of the disclosed embodiments may include pole magnets that are formed of two or more parts, one of which is permanently bonded via weld or braze, for example to the insert wall (e.g., the "coupling portion") and another which includes windings (e.g., the "winding portion"). The coupling portion may undergo manufacturing steps, such as brazing, annealing and degassing, that are performed at relatively high temperatures. In contrast, the winding portion, which may include temperature sensitive features such as windings and magnetic materials, may be coupled to the coupling portion after the high temperature manufacturing steps are complete, so as not to exceed temperatures that may damage those features (e.g., the coil insulation temperature limit and the melting point).

Figure 3E:
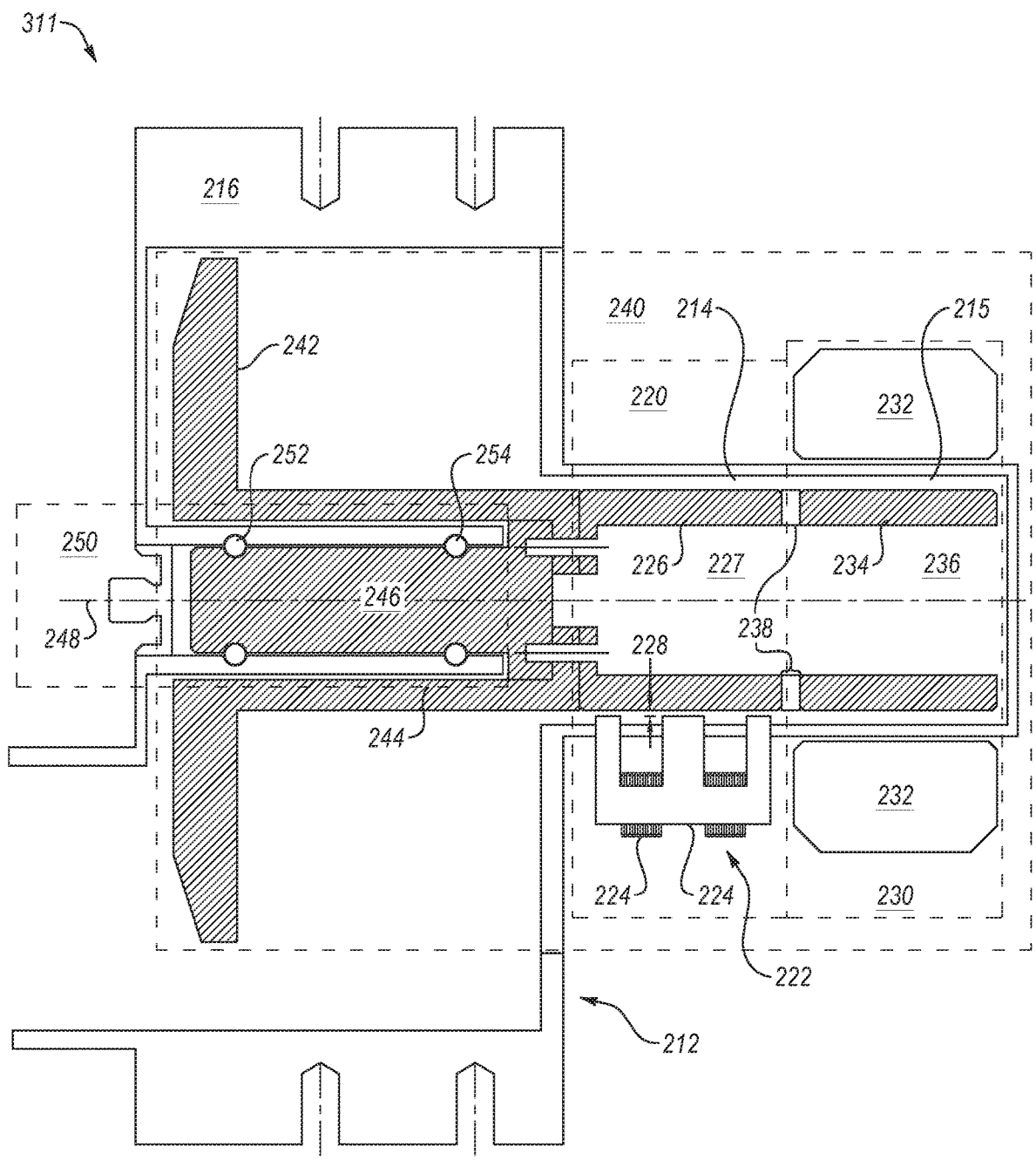
FIG. 3E illustrates a side cross section view of another example of an X-ray source.

FIG. 3E illustrates a side cross section view of another example of an X-ray source 311. The X-ray source 311 may include any suitable features described above with respect to the X-ray source 310, and similar features are indicated with the similar numbering. As shown in FIG. 3E, in some configurations, the position of the motor assembly 230 and the lift assembly 220 may be switched. In such configurations, the lift assembly 220 may be positioned adjacent to the bearing assembly 250, closer to the anode assembly 240 than the motor assembly 230.

FIG. 4 illustrates a perspective view of a lift electromagnet 350. The lift electromagnet 350 may be incorporated into an X-ray source, such as the X-ray source 310 of FIG. 3D, or the X-ray source 311 of FIG. 3E. Accordingly, the lift electromagnet 350 may include any suitable features described with respect to the lift electromagnet 322 of FIG. 3D, or vice versa. As illustrated, the lift electromagnet 350 is integrated into an insert wall 352. The insert wall 352 may separate an interior 354 of the insert wall 352 from an exterior 356. The insert wall 352 may define a vacuum envelope that may permit the interior 354 to be evacuated.

The lift electromagnet 350 includes a core 355 and with three poles 360, 362, and 364. As illustrated, the poles 360, 362, and 364 may form an "M" or "W" shape. The lift electromagnet 350 may include windings, coils or wires (not shown) wrapped around winding portions 366, 368, 370 of the core 355. In addition, the lift electromagnet 350 may include coupling portions 363, 365, and 367 that extend through the insert wall 352 from the exterior 356 of the insert wall 352 to the interior 354. The coupling portions 363, 365, 367 may include plugs, patches or inserts coupled to the insert wall 352. Each of the coupling portions 363, 365, 367 may correspond in size, shape, and position to one of the winding portions 366, 368, 370 of the poles 360, 362, 364.

The coupling portions 363, 365, 367 may be secured to the insert wall 352, for example, by brazing or welding, to embed the poles in the insert wall 352. In some configurations, a braze joint may be positioned between the coupling portions 363, 365, 367 to the insert wall 352 to the hermetically seal the interior 354 from the exterior 356. In some configurations, each corresponding pair of the coupling portions 363, 365, 367 and the winding portions 366, 368, 370 may be referred to as a vacuum penetrating pole assembly.

In some configurations, the material of the coupling portions 363, 365, 367 may be selected to be suitable for brazing to the insert wall 382. Additionally or alternatively, since the coupling portions 363, 365, 367 may be positioned at least partially inside of a vacuum, the material of the coupling portions 363, 365, 367 may be selected to avoid contaminating or decreasing the quality of the vacuum. In contrast, in some configurations the winding portions 366, 368, 370 are not brazed and are not positioned in the vacuum, so other suitable materials may be implemented. Thus, in some embodiments, different materials may be used for the coupling portions 363, 365, 367 and the winding portions 366, 368, 370. For example, the material of the winding portions 366, 368, 370 may have relatively high magnetic permeability, but may not necessarily be suitable for brazing or to be positioned inside of the vacuum. In some embodiments, the material of the winding portions 366, 368, 370 may have a higher magnetic permeability than the coupling portions 363, 365, 367. Additionally or alternatively, the materials of the coupling portions 363, 365, 367 may be selected based on its thermal expansion characteristics. For example, the material of the coupling portions 363, 365, 367 may be selected to have a similar thermal expansion coefficient as the insert wall 382 and/or braze material so the components are not deformed or damaged when the materials change in temperature.

Figure 5:
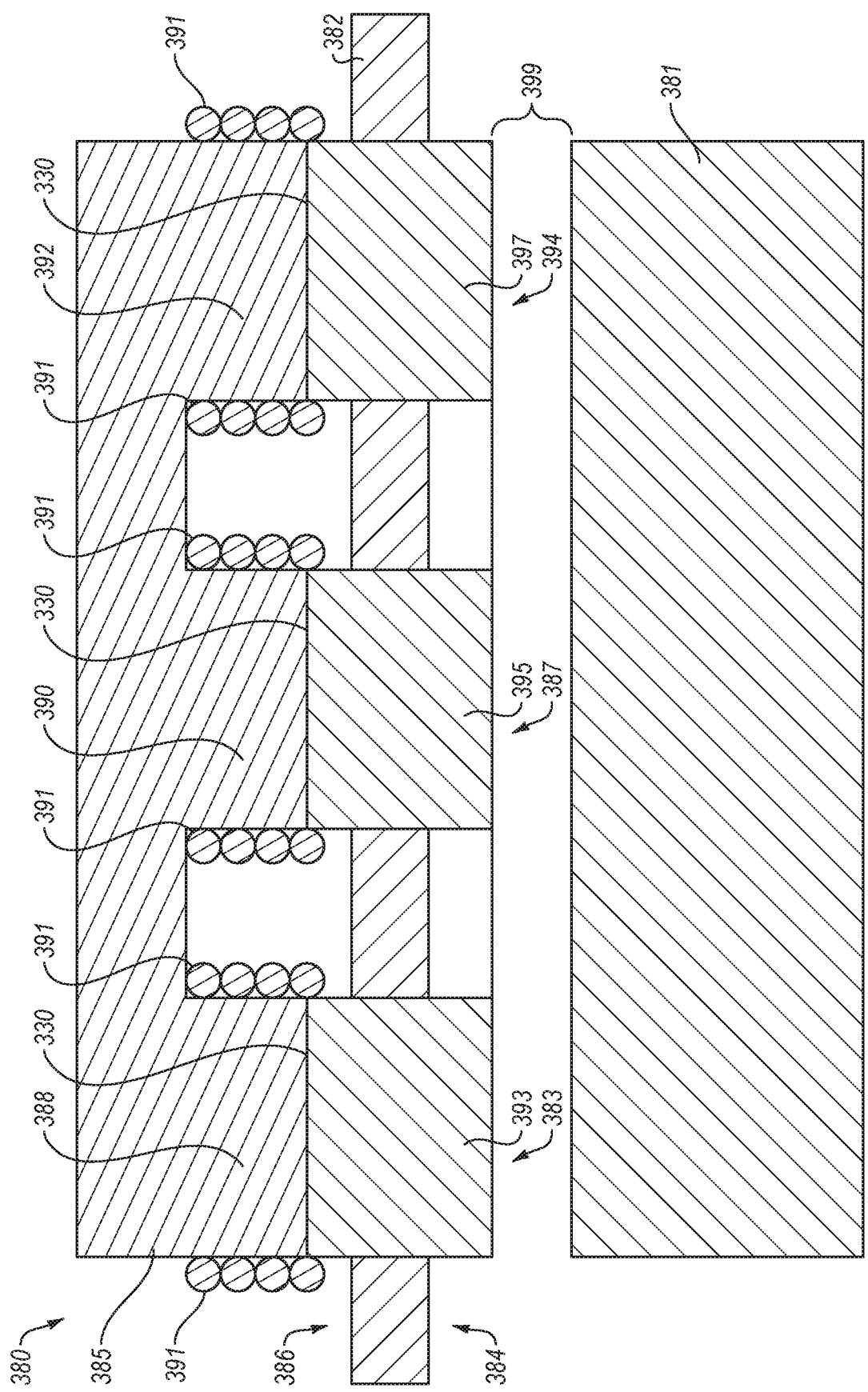
FIG. 5 illustrates a side cross section schematic view of another example of a lift electromagnet that may be implemented in an X-ray source.

The coupling portions 363, 365, 367 may include a ferromagnetic material, such as a low carbon steel, high purity iron, cobalt-iron, nickel-iron, or other suitable material. The insert wall 352 may be formed of a nonmagnetic material, such as stainless steel or ceramic. The winding portions 366, 368, 370 may be formed of ferromagnetic material, such as a low carbon steel, high purity iron, cobalt-iron, nickel-iron, or other suitable material. The braze between the coupling portions 363, 365, 367 and the insert wall 352 may include copper, gold, nickel, silver, palladium, various alloys thereof, or any other suitable braze material. In some configurations, the material of the coupling portions 363, 365, 367, the winding portions 366, 368, 370, and/or the insert wall 352 may be selected to include similar coefficients of thermal expansion. FIG. 5 illustrates a side cross section schematic view of another example of a lift electromagnet 380. The lift electromagnet 380 may include suitable aspects described with respect to the lift electromagnet 350, such as a core 385 and with three poles 383, 387, 394, each including a corresponding coupling portion 393, 395, 397 and winding portion 388, 390, 392. As shown, an insert wall 382 separates an interior 384 from an exterior 386, and the coupling portions 393, 395, and 397 extend through the insert wall 382. The coupling portions 393, 395, and 397 are coupled with the insert wall 382 thereby sealing the interior 384 from the exterior 386, and permitting the interior 384 to be evacuated. As shown, windings 391 may be wrapped around the winding portions 388, 390, 392 of the core 855 between the poles 383, 387, 394.

In the illustrated configurations, the windings 391 are positioned proximate an interface 330 between the coupling portions 393, 395, and 397 and the winding portions 388, 390, 392. In particular, the windings 391 extend over the interface 330 between the coupling portions 393, 395, and 397 and the winding portions 388, 390, 392, although other configurations may be implemented.

As shown in FIG. 5, the lift electromagnet 380 may be positioned proximate a lift shaft 381, to exert a lifting force on the lift shaft 381. Since the coupling portions 393, 395, and 397 of the poles 383, 387, 394 extend through the insert wall 382, they may be positioned closer to the lift shaft 381. Accordingly, a lift gap 399 between the poles 383, 387, 394 and the lift shaft 381 may be smaller when compared to other configurations, such as the configuration shown in FIG. 3C, where the lift assembly 220 as positioned fully outside of the insert wall 214. In the configuration illustrated in FIG. 3F, the lift gap 399 may be reduced to a distance of 1 mm or smaller.

Figure 6:
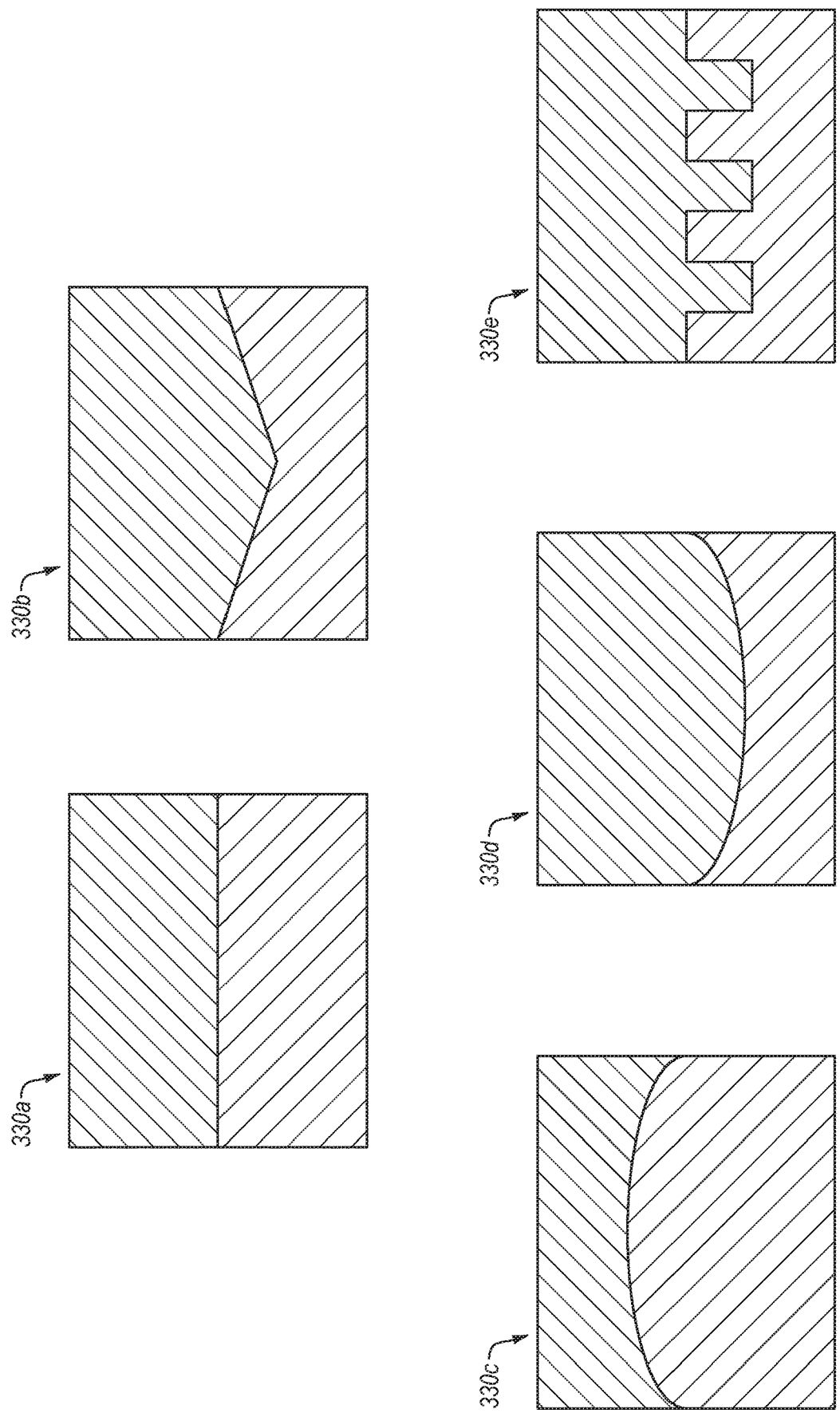
FIG. 6 illustrates side cross section schematic views of interfaces that may be implemented between the coupling portions and the winding portions.

In the configuration of FIG. 5, the interface 330 between the coupling portions 393, 395, and 397 and the winding portions 388, 390, 392 is substantially planar. However, other configurations may be implemented, as shown, for example, in FIG. 6. FIG. 6 illustrates side cross section schematic views of interfaces 330a-e that may be implemented between the coupling portions and the winding portions described above. Configuration 330a illustrates a substantially planar interface, such as the interface 330 of FIG. 5. In configuration 330b, the interface is positioned on two planes, in substantially a V-shape, cone, or corner shape. In configurations 330c and 330d, the interface is not planar, and instead is curved. In configuration 330e, the interface includes teeth or knobs that interface with one another. In the configuration 330a, the coupling portions and the winding portion may be moved with respect to one another until they are permanently or removably fixed. In contrast, the corners, curvature, or knob features of the configurations 330b-e may retain the coupling portions and the winding portion with respect to one another (at least in one dimension). Such configurations may assist in aligning the coupling portion with the winding portion, and/or fixing the coupling portion to the winding portion. Although FIG. 6 illustrates two-dimensional cross sectional views, it should be appreciated that the interfaces may include any suitable three-dimensional configuration that retain the coupling portions and the winding portion with respect to one another.

Figure 7A:
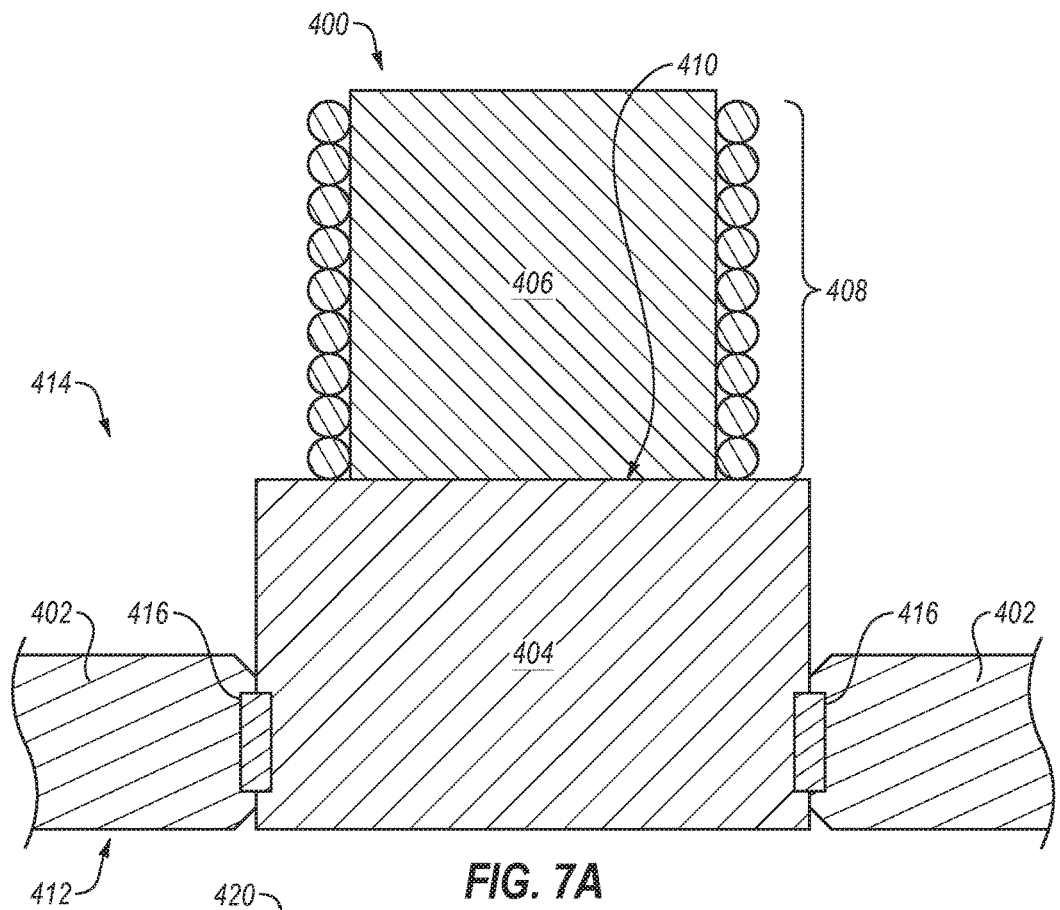
FIGS. 7A-7E illustrate side cross section views of examples of pole inserts that may be implemented in a lift electromagnet.

FIG. 7A illustrates a side cross section schematic view of an example of a pole insert 400 that may be implemented in an X-ray source, such as the X-ray source 310 of FIG. 3D or the X-ray source 311 of FIG. 3E, or in the lift electromagnets 350, 380 of FIGS. 4-5. As illustrated, the pole insert 400 may be positioned in an insert wall 402. The pole insert 400 includes a coupling portion 404 and a winding portion 406.

The coupling portion 404 may be brazed or welded to the insert wall 402, thereby forming a hermetic seal. In some configurations, a braze material 416 (e.g., copper or other suitable braze material) may be positioned between the coupling portion 404 and the insert wall 402. The braze material 416 may be heated and melted to form a braze bond between the coupling portion 404 and the insert wall 402. In other configurations, the coupling portion 404 may be welded to the insert wall 402. However, any suitable coupling configuration may be implemented to couple the coupling portion 404 and the insert wall 402.

The insert wall 402 may separate an interior 412 of the insert wall 402 from an exterior 414. The coupling portion 404 may seal an opening defined by the insert wall 402, thereby permitting the interior 412 to be evacuated. After high temperature manufacturing steps are complete, the winding portion 406 may be coupled to the coupling portion 404 and/or windings 408 may be positioned around at least a portion of the pole insert 400.

The winding portion 406 may be permanently or removably coupled with the coupling portion 404. In some configurations, the winding portion 406 may be positioned against or press-fit against the coupling portion 404 to retain the winding portion 406 with the coupling portion 404. In other configurations, the winding portion 406 may be coupled with the coupling portion 404 using an adhesive or a mechanical coupling, or any other suitable coupling configuration. The adhesive, mechanical coupling, or other suitable coupling configuration may maintain structural integrity at the operating conditions of the X-ray source (e.g., high temperatures).

As illustrated, the windings 408 may be positioned around the winding portion 406 at or proximate an interface 410 between the coupling portion 404 and the winding portion 406. In such configurations, the windings 408 may direct the magnetic field to the coupling portion 404 and/or to the end of the pole insert 400 proximate the lift shaft. The windings 408 may be positioned around the winding portion 406 before or after the winding portion 406 is coupled to the coupling portion 404, but generally after the high temperature manufacturing steps are complete.

In the illustrated configuration of the pole insert 400, components that may be temperature-sensitive, such as the winding portion 406 and/or windings 408 are coupled to the coupling portion 404 after high temperature manufacturing steps are complete so as not to exceed temperatures that may damage those features (e.g., the coil insulation temperature limit).

In the configuration of FIG. 7A, the winding portion 406 is positioned over the coupling portion 404, and includes at least one dimension (e.g., length or width) that is smaller than a corresponding dimension of the coupling portion 404. Such configurations of the coupling portion 404 may facilitate in ensuring that the coupling portion 404 does not saturate at lower applied current than the rest of the pole insert 400. Accordingly, the cross-sectional area of the coupling portion 404 may be at least as large as the cross-sectional area of the winding portion 406.

Figure 7B:
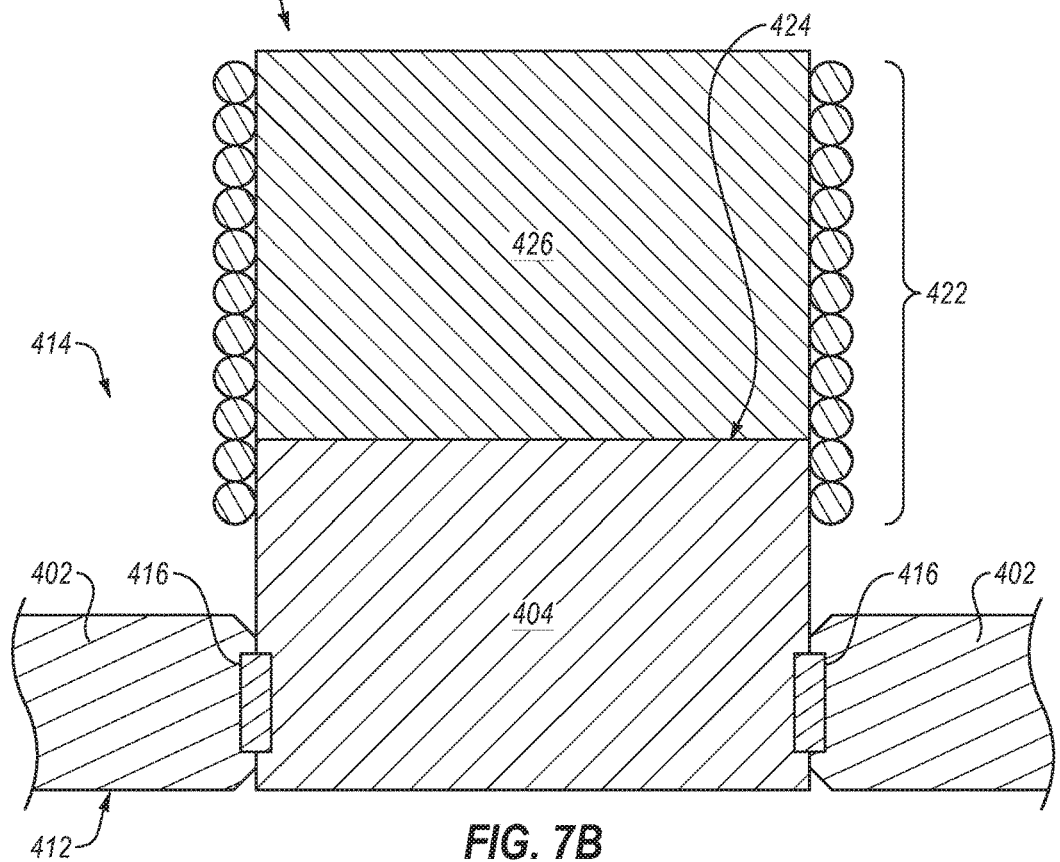

FIG. 7B illustrates a side cross section view of another example of a pole insert 420 that may be implemented in an X-ray source, such as the X-ray source 310 of FIG. 3D or the X-ray source 311 of FIG. 3E. This configuration includes a winding portion 426 with at least one dimension (e.g., length or width) that corresponds with and/or is substantially the same size as a dimension of the coupling portion 404. While the windings 408 of FIG. 7A extend over the winding portion 406 generally to the interface 410, in the configuration of FIG. 4B, windings 422 are positioned around both the winding portion 426 and at least part of the coupling portion 404. In such configurations, the windings 422 extend to fully cover an interface 424 between the winding portion 426 and the coupling portion 404. In such configurations, the windings 422 may direct the magnetic field to the coupling portion 404 and/or to the end of the pole insert 420 proximate the lift shaft. In some circumstances, positioning the windings 422 to extend to fully cover the interface 424 may improve containment of the magnetic field to the coupling portion 404 and/or to the end of the pole insert 420.

In the configurations of FIGS. 7A and 7B, the pole inserts 400, 420 include substantially rectangular cross sections at the interface. In particular, the winding portions 406, 426 and the coupling portion 404 are substantially rectangular in cross section. However, pole inserts may have any suitable configurations and features. For example, pole inserts may include alignment or fixturing features that may facilitate: positioning the pole insert with respect to the insert wall, positioning the winding portion with respect to the coupling portion, and/or containing braze or flux material. Such configurations will be described with respect to FIGS. 4C-4G below.

Figure 7C:
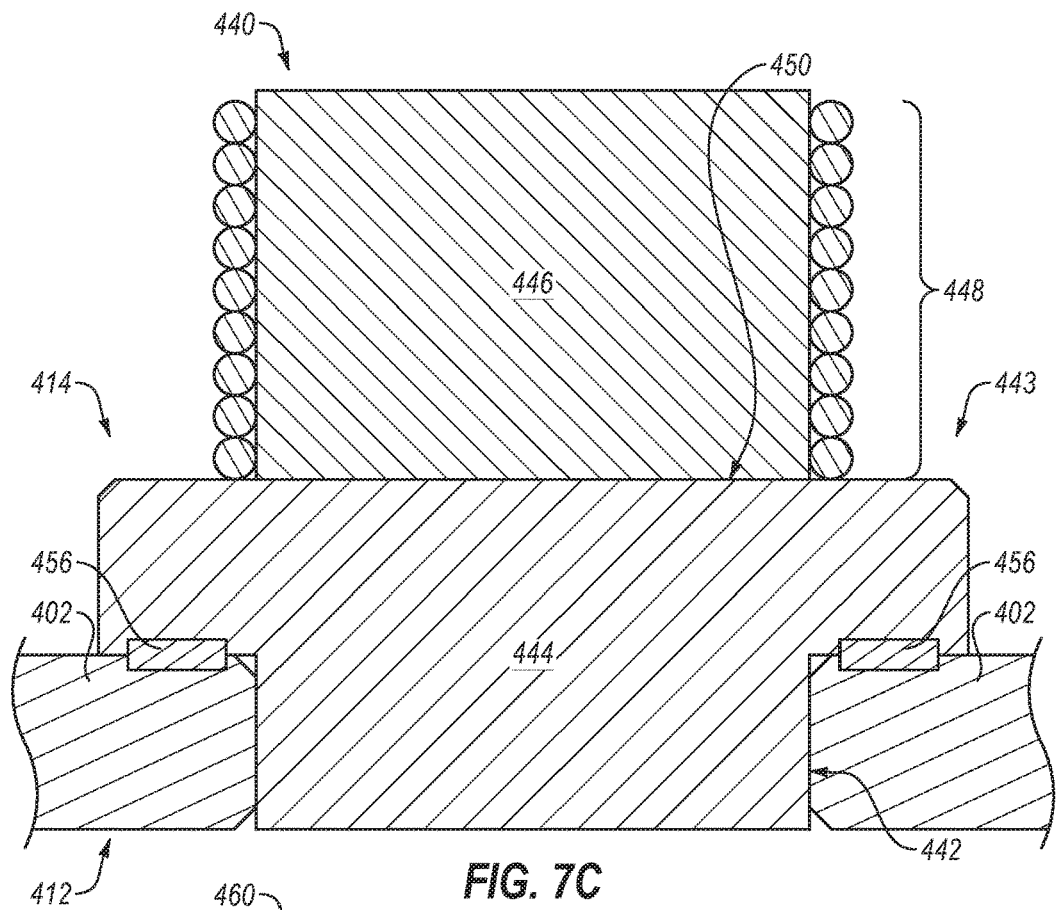

FIG. 7C illustrates a side cross section view of another example of a pole insert 440 that may be implemented in an X-ray source, such as the X-ray source 310 of FIG. 3D or the X-ray source 311 of FIG. 3E. As shown, the pole insert 440 includes a winding portion 446 and a coupling portion 444 that may include any suitable features described above. Windings 448 may be positioned around the winding portion 446 at or proximate an interface 450 between the coupling portion 444 and the winding portion 446.

However, in the illustrated configuration the coupling portion 444 extends between a lower portion 442 and an upper portion 443. As shown, the lower portion 442 is sized and shaped to be positioned in an opening defined by the insert wall 402, and the upper portion 443 is wider than or includes at least one dimension greater than the lower portion 442. In such configurations, the upper portion 443 defines a flange or rim that facilitates in positioning the coupling portion 444 in the opening defined by the insert wall 402, and retains the coupling portion 444 when it is positioned inside of the opening. The flange defined by the coupling portion 444 may facilitate in positioning and/or aligning the pole insert 440 with respect to the insert wall 402, and may be referred to as an alignment or fixturing feature.

A braze material 456 (e.g., copper or other suitable braze material) may be positioned between the coupling portion 444 and the insert wall 402. As shown, the braze material 456 may be positioned between a top surface of the insert wall 402 and a bottom surface of the pole insert 440. In particular, the braze material 456 is positioned between the flange of the upper portion 443 of the pole insert 440 and the top surface of the insert wall 402. Such configurations may facilitate in retaining the braze material 456 at the interface between the insert wall 402 and the pole insert 440. Additionally or alternatively, the pole insert 440 may include a recess or protrusion positioned at or proximate the position of the braze material 456 to facilitate in retaining the braze material in position.

Figure 7D:
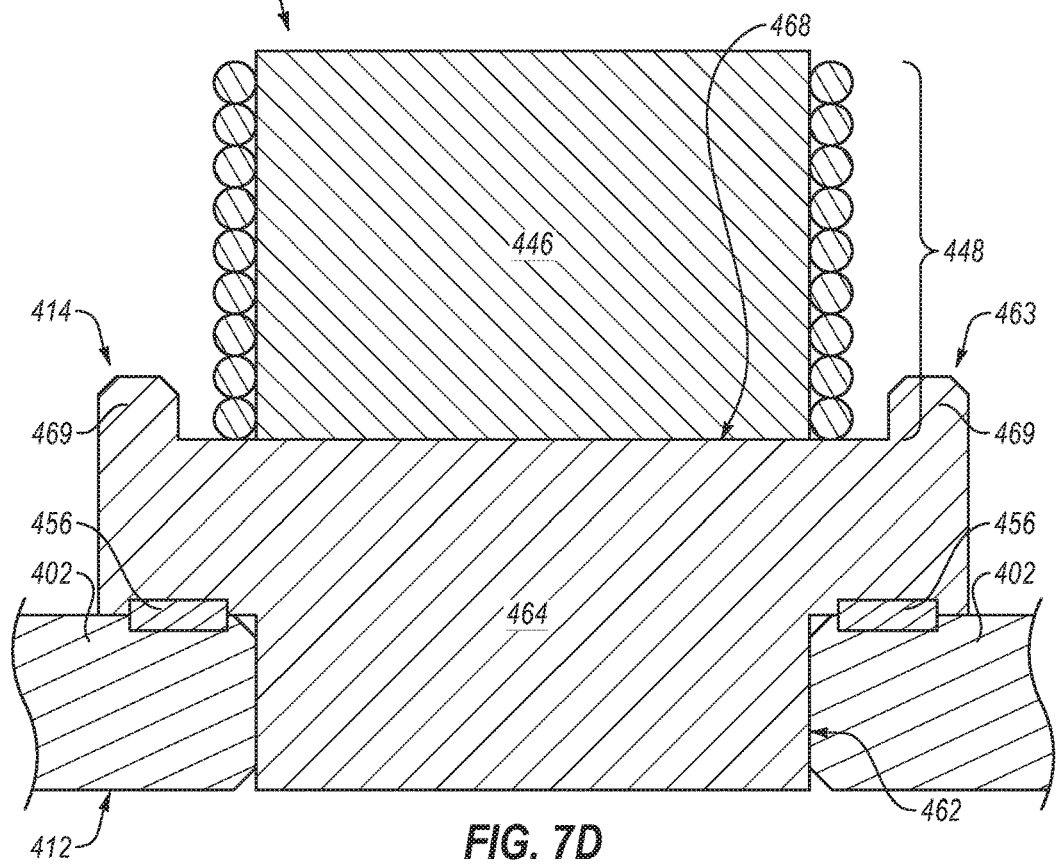

FIG. 7D illustrates a side cross section view of another example of a pole insert 460 that may be implemented in an X-ray source, such as the X-ray source 310 of FIG. 3D or the X-ray source 311 of FIG. 3E. The pole insert 460 may generally include the features described above with respect to the pole insert 440 of FIG. 7C. The pole insert 460 includes a coupling portion 464 that extends between a lower portion 462 and an upper portion 463, and the upper portion 463 defines an opening 468 that is sized and shaped to receive the winding portion 446.

The upper portion 463 also defines flanges 469 that extend above a bottom of the winding portion 446. The opening 468 and/or the flanges 469 may facilitate in positioning and/or aligning the coupling portion 464 with respect to the winding portion 446, and may be referred to as an alignment or fixturing feature. Additionally or alternatively, the flanges 469 extend above an interface 450 between the coupling portion 464 and the winding portion 446, and may facilitate in containing and/or positioning the windings 448. Further, in some configurations the flanges 469 may facilitate in directing the magnetic field generated by the pole insert 460 as it is directed to a lift shaft.

Figure 7E:
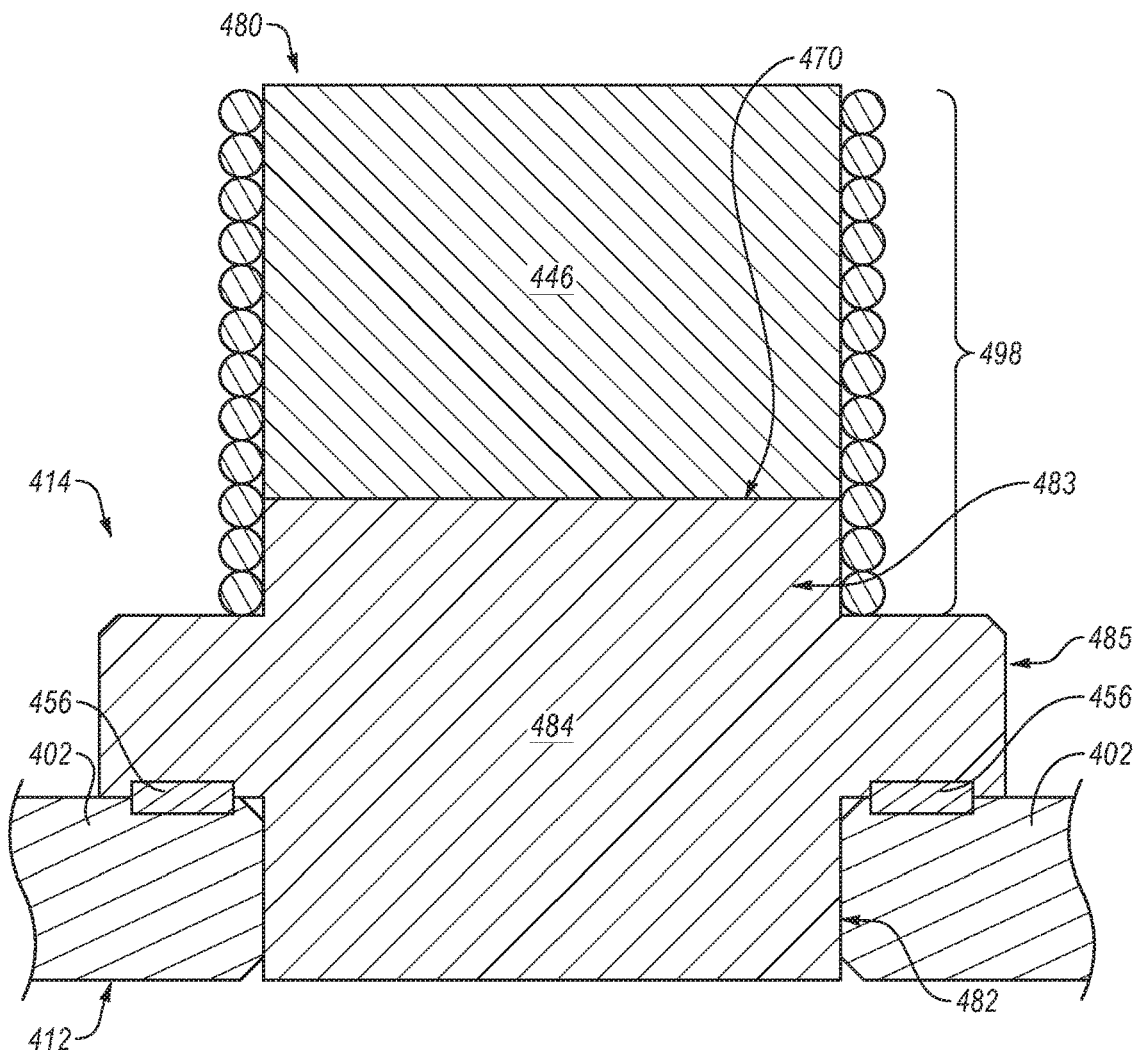

FIG. 7E illustrates a side cross section view of another example of a pole insert 480 that may be implemented in an X-ray source, such as the X-ray source 310 of FIG. 3D or the X-ray source 311 of FIG. 3E. The pole insert 480 may generally include the features described above with respect to the pole inserts 440, 460 of FIGS. 7C and 7D. However in FIGS. 7C and 7D, the upper portions of the coupling portions 444, 464 are wider than or include at least one dimension larger than a corresponding dimension of the winding portion 446. In contrast, in the illustrated configuration an upper portion 483 of coupling portion 484 is substantially the same size as the winding portion 446.

In such configurations, the coupling portion 484 includes a substantially t-shaped or cross-shaped cross section. The coupling portion 484 includes an intermediary portion 485 that includes at least one dimension that is greater than a corresponding dimension of the upper portion 483 and a lower portion 482. The lower portion 482 is sized and shaped to be received in the opening defined by the insert wall 402. The intermediary portion 485 defines a flange or rim that facilitates in positioning the pole insert 480 in the opening defined by the insert wall 402, and retains the pole insert 440 when it is positioned inside of the opening.

In the configuration illustrated in FIG. 7E, windings 498 may be positioned around both the winding portion 446 and at least part of the coupling portion 484. In such configurations, the windings 498 extend to fully cover an interface 490 between the winding portion 446 and the coupling portion 484. In some configurations, the windings 498 may be positioned against the flange defined by the intermediary portion 485, which may facilitate in retaining the windings 498 in place.

In some configurations, windings may be formed on a mandrel or a form. In one example, the mandrel or form may correspond in size and shape to the winding portion, the coupling portion, or both. The windings may be wound around the mandrel or form to a desired shape, and the windings may be positioned around the winding portion and/or the coupling portion. In some aspects, the windings may surround the interface between the winding portion and the coupling portion. For example, the windings 498 may be formed on a mandrel or form, and may be positioned to surround the interface 490 as well the winding portion 446 and at least part of the coupling portion 484. Although such configurations may be implemented in other embodiments as well.

Figure 7F:
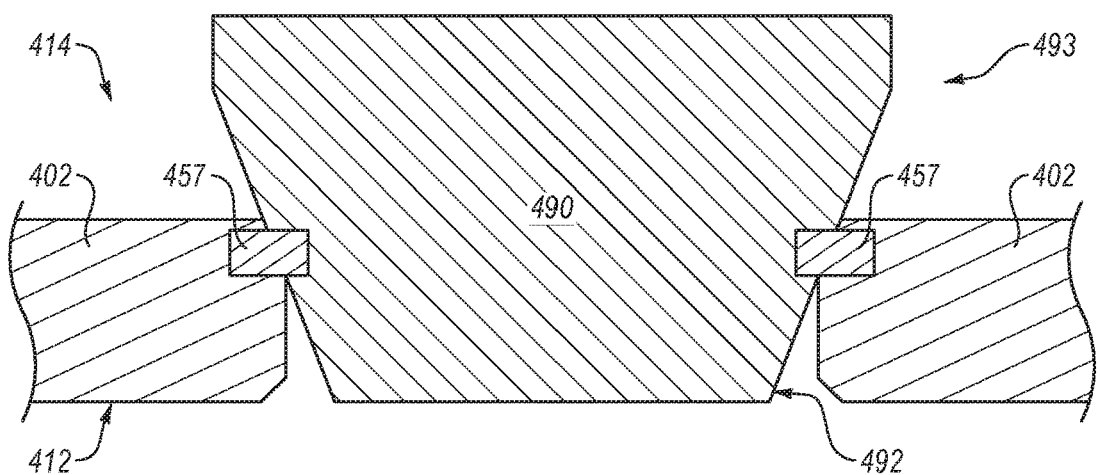
FIG. 7F illustrates a side cross section view of an example of a coupling portion that may be implemented in a pole insert.

FIG. 7F illustrates a side cross section view of an example embodiment of a coupling portion 490 for a pole insert. The coupling portion 490 may be implemented in any of the pole inserts described above. As illustrated, the coupling portion 490 includes a taper extending between a lower portion 492 and an upper portion 493. The lower portion 492 is sized and shaped to be positioned in an opening defined by the insert wall 402, while the upper portion 493 is larger than the opening, thereby facilitating in positioning the coupling portions 490 in the opening defined by the insert wall 402, and retaining the coupling portions 490 when it is positioned inside of the opening. The taper defined by the coupling portion 490 may facilitate in positioning and/or aligning the coupling portion 490 with respect to the insert wall 402, and may be referred to as an alignment or fixturing feature. A braze material 457 (e.g., copper or other suitable braze material) may be positioned between the coupling portion 490 and the insert wall 402, and the coupling portion 490 and the insert wall 402 may be brazed to one another.

In the configurations illustrated in FIGS. 7A-7F, the coupling portions and the winding portions include, for example, rectangular or trapezoidal cross sections. However, the coupling portions and the winding portions may include round, oval, or other suitably shaped configurations. For example, FIG. 3E illustrates a configuration where the coupling portions and the winding portions include a rectangular shape with rounded corners. Other configurations may be implemented while incorporating the concepts described herein.

In other configurations, pole inserts may include recesses positioned to contain braze or flux materials before or during brazing or other coupling processes. Such recesses may be positioned at or proximate the positions where the braze materials are shown in the configurations describe above. Furthermore, pole inserts may include protrusions and corresponding recesses to position or align coupling portions and the winding portions with respect to one another. For example, the coupling portion may include a protrusion and the winding portion may include a corresponding recess sized and shaped to facilitate positioning or aligning of the coupling portion with respect to the winding portion, or vice versa. Similarly, pole inserts and insert walls may include protrusions and corresponding recesses to position or align the pole inserts and the insert wall with respect to one another. For example, the coupling portion may include a protrusion and the insert wall may include a corresponding recess sized and shaped to facilitate positioning or aligning of the coupling portion with respect to the winding portion, or vice versa.

The pole inserts and/or the lift electromagnets may be manufactured in any suitable manner to implement the concepts described herein. In one example, the various parts, such as the coupling portions and/or the winding portions may be formed by machining. The parts may be cleaned to remove contaminants and other undesirable materials. The parts may then be brazed to one another. In particular, the coupling portion may be brazed to the insert wall, as described above. The joint between the insert wall and the coupling portion may be visually inspected and/or may be tested to verify that it is properly hermetically sealed and is capable of retaining a vacuum. The parts, such as the coupling portion, may be further machined to a desired configuration. For example, in some configurations the coupling portion may be machined to a desired flatness, for example, to interface with the winding portion. Additionally or alternatively, the coupling portion may be machined to create an opening or recess to receive or mate with the winding portion, or one or more flanges to facilitate aligning the winding portion with the coupling portion.

In some configurations, the pole inserts and/or the lift electromagnets may be supported by a fixture during manufacture. For example, the pole inserts and/or the lift electromagnets may be supported by a support that includes, for example graphite. A weight or a force may be applied on one or more of the inserts during the brazing process to position, for example, the coupling portion against the insert wall with braze material positioned in between.

Figure 8A:
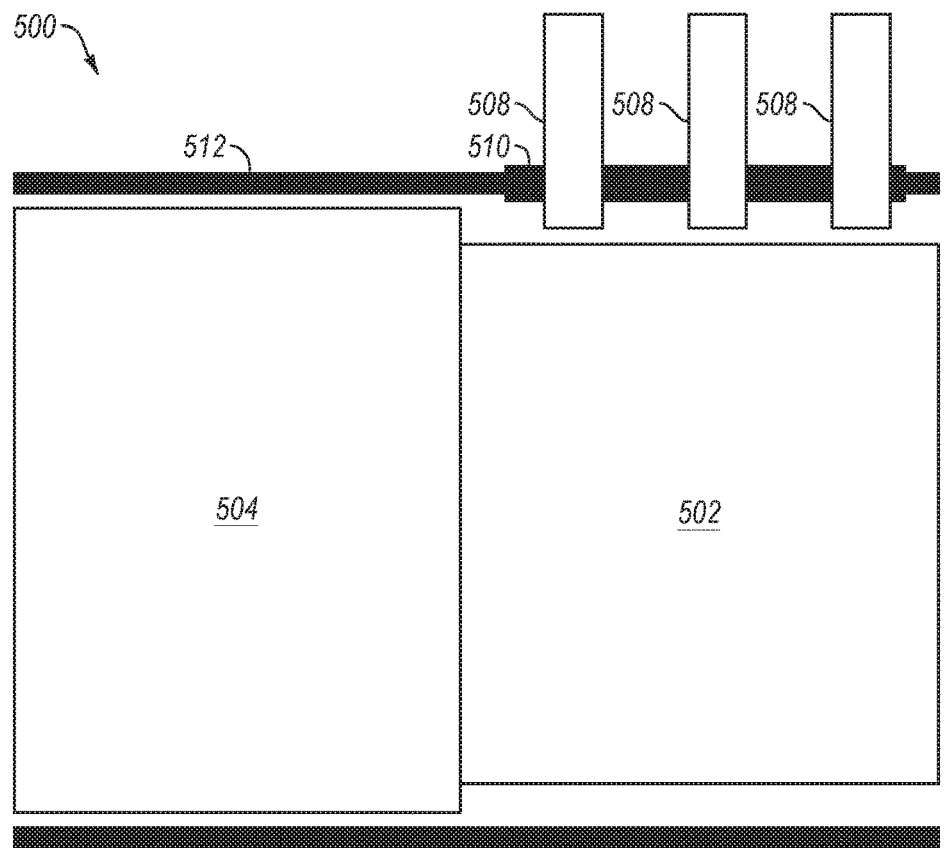
FIG. 8A illustrates a side cross section view of another example embodiment of a lift electromagnet.

In the configurations of FIGS. 7A-7F, the pole inserts may include plugs, patches, or inserts (e.g., coupling portions) that are directly coupled to the insert wall. However, in other configurations, the pole inserts may instead be coupled to a wall insert which may then be coupled to the insert wall. Such configurations may simplify the manufacturing process, for example, by simplifying the machining that may be necessary for the parts involved. Furthermore, one wall insert may be used for all of the pole inserts, rather than having separate coupling portions for each pole insert, as illustrated in the configurations of FIGS. 7A-7F. FIG. 8A illustrates an example of such a configuration.

FIG. 8A illustrates a side cross section view of an example embodiment of a lift electromagnet 500. As illustrated, the lift electromagnet 500 includes three pole inserts 508 coupled to a wall insert 510. The pole inserts 508 extend through the wall insert 510 and terminate proximate a lift shaft 502. An insert wall 512 may at least partially define a vacuum envelope, and may surround the lift shaft 502 and a rotor 504, which may be part of a motor assembly that rotates an anode. The wall insert 510 may be coupled to the insert wall 512. For example, the pole inserts 508 may be brazed or welded to the wall insert 510. In some configurations, the pole inserts 508 may be coupled to the wall insert 510 before the wall insert 510 is coupled to the insert wall 512. The wall insert 510 may then be coupled to the insert wall 512, for example, by brazing or welding.

The configuration of the lift electromagnet 500 may simplify the manufacturing process, for example, by simplifying the machining that may be necessary for the parts involved. In particular, the wall insert 510 may be fabricated before it is coupled to the insert wall 512 and/or the pole inserts 508 may be coupled to the wall insert 510 before it is coupled to the insert wall 512. The wall insert 510, along with the pole inserts 508, may then be coupled to the insert wall 512. Furthermore, a single wall insert 510 may be used for all of the pole inserts 508, rather than having separate coupling portions for each pole insert as illustrated in the configurations of FIGS. 7A-7F.

In some configurations, the pole inserts 508 may not require separate coupling portions and winding portions. Instead, the pole inserts 508 may extend through and may be coupled to the wall insert 510. In other configurations, each of the pole inserts 508 may include coupling portions coupled to the wall insert 510, for example, as described above with respect to FIGS. 7A-7F. The wall insert 510 may then be coupled to the insert wall 512.

Figure 8B:
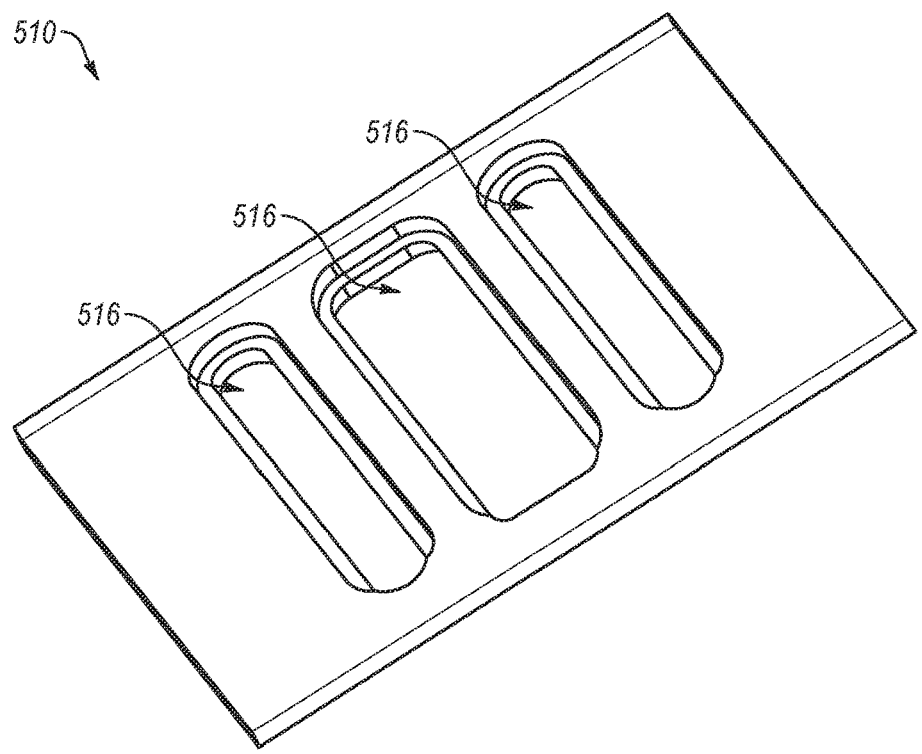
FIG. 8B illustrates a perspective view of an example embodiment of a vacuum wall insert that can be implemented in a lift electromagnet.

FIG. 8B illustrates a perspective view of an example embodiment of a wall insert 510 that may be implemented in the lift electromagnet 500 of FIG. 8A. As illustrated, the wall insert 510 may include openings 516 sized and shaped to receive each pole insert of a lift electromagnet. The pole inserts may be positioned in the openings 516, and may be coupled to the wall insert 510 by brazing or welding.

Figure 9A:
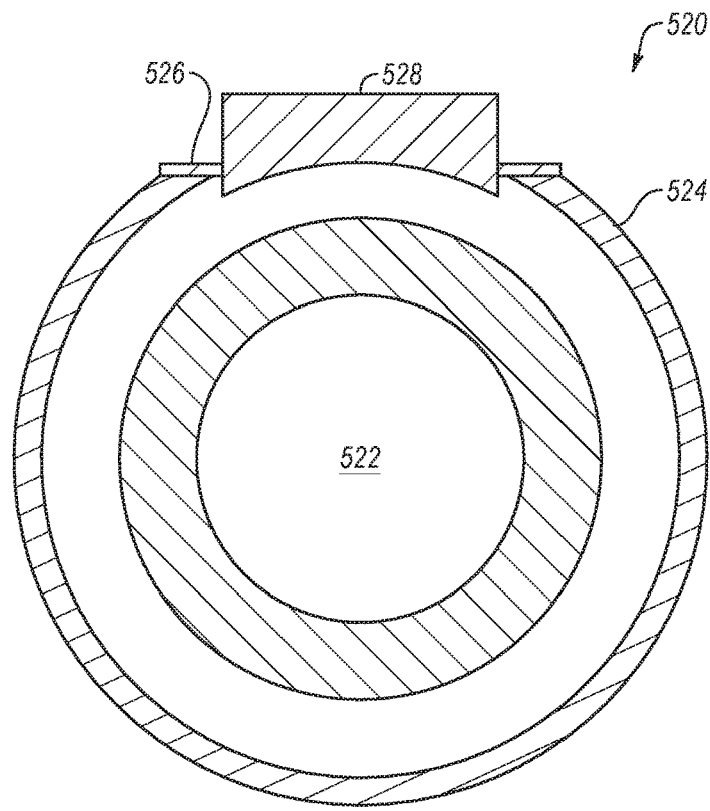
FIGS. 9A-9B illustrate cross section views of example embodiments of lift electromagnets.

As shown, for example, in FIG. 3B, the lift shaft 226 may be substantially cylindrical and may include an annular cross section. Accordingly, the insert wall 214 and/or wall inserts proximate the lift assembly 220 may be cylindrical and may include an annular cross section to correspond to and receive the lift shaft 226. Thus, in some configurations the lift assemblies and the pole inserts described herein may include rounded or contoured configurations to correspond to the curvature of the insert wall. For example, the coupling portions described herein may include curved or contoured surfaces on the interior of the insert wall. The curved or contoured surfaces may correspond to the curvature of a lift shaft of a lift assembly, thereby permitting the pole insert to be positioned close to the lift shaft to exert a greater force of the lift shaft. FIG. 9A illustrates an example of such a configuration.

FIG. 9A illustrates a cross section view of another example embodiment of a lift electromagnet 520. As illustrated, the lift electromagnet 520 includes a wall insert 526 positioned in an insert wall 524 that surrounds a lift shaft 522. As shown, in some configurations the lift shaft 522 may be hollow, tube-shaped and/or may have an annular cross-section to reduce mass. The wall insert 526 may be coupled to the insert wall 524. A pole insert 528 may extend through the wall insert 526 and may be coupled to the wall insert 526. The insert wall 524, the wall insert 526, and the pole insert 528 may be coupled to one another via brazing or welding (or equivalent). The pole insert 528 extends through the wall insert 526 and terminates proximate a lift shaft 522.

As shown, the insert wall 524 is cylindrical and includes an annular cross section that corresponds to the lift shaft 522. The pole insert 528 includes a rounded or contoured configuration to correspond to the curvature of the insert wall 524. In particular, the pole insert 528 includes a curved or contoured surface on the interior of the insert wall 524. The curved or contoured surfaces may correspond to the curvature of the lift shaft 522, thereby permitting the pole insert 528 to be positioned close to the lift shaft 522 to exert a greater force of the lift shaft 522. The wall insert 526 may be substantially planar, such as the wall insert 514 of FIG. 5B. Such configurations may facilitate coupling and positioning of the wall insert 526 and the insert wall 524 with respect to one another. Although the view shown in FIG. 5C includes one pole insert 528, the configuration of the pole insert 528 may be included in any and all of the pole inserts of a lift electromagnet. In addition, the configuration of the pole insert 528 may be included in any of the embodiments described above.

Figure 9B:
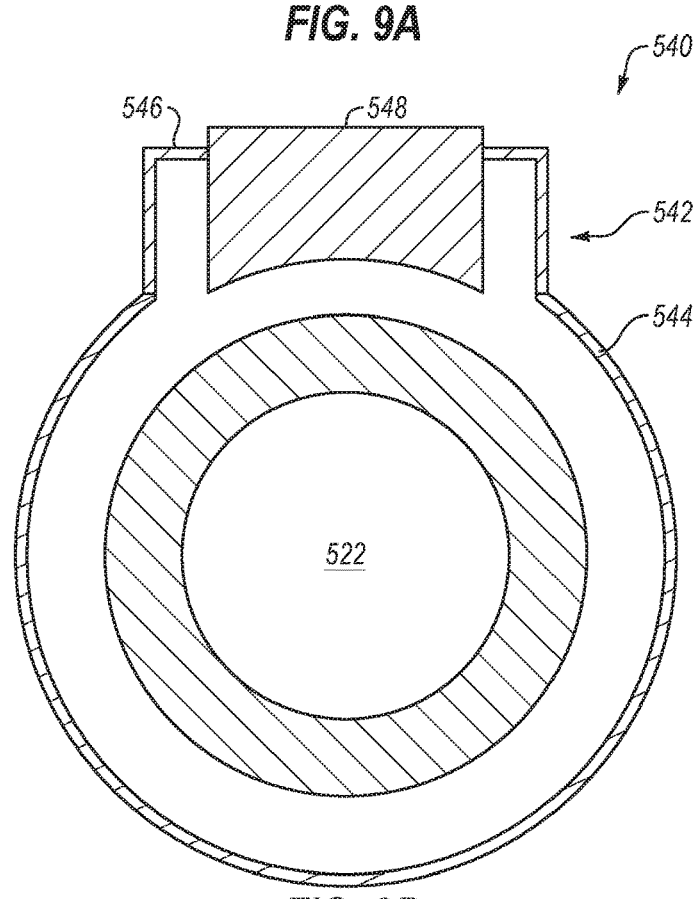

FIG. 9B illustrates a cross section view of another example embodiment of a lift electromagnet 540. In the illustrated configuration, an insert wall 544 may include a saddle joint 542. In such configurations, a wall insert 546 may be coupled to the insert wall 544 proximate the saddle joint 542. The pole insert 548 extends through the wall insert 544 and terminates proximate the lift shaft 522.

The pole insert 548 includes a rounded or contoured configuration to correspond to the curvature of the lift shaft 522. In particular, the pole insert 548 includes a curved or contoured surface on the interior of the insert wall 544. The curved or contoured surfaces may correspond to the curvature of the lift shaft 542, thereby permitting the pole insert 548 to be positioned close to the lift shaft 542 to exert a greater force of the lift shaft 542. The wall insert 546 may be substantially planar, such as the wall insert 514 of FIG. 5B. Such configurations may facilitate coupling and positioning of the wall insert 546 and the insert wall 544 with respect to one another.

Figure 10A:
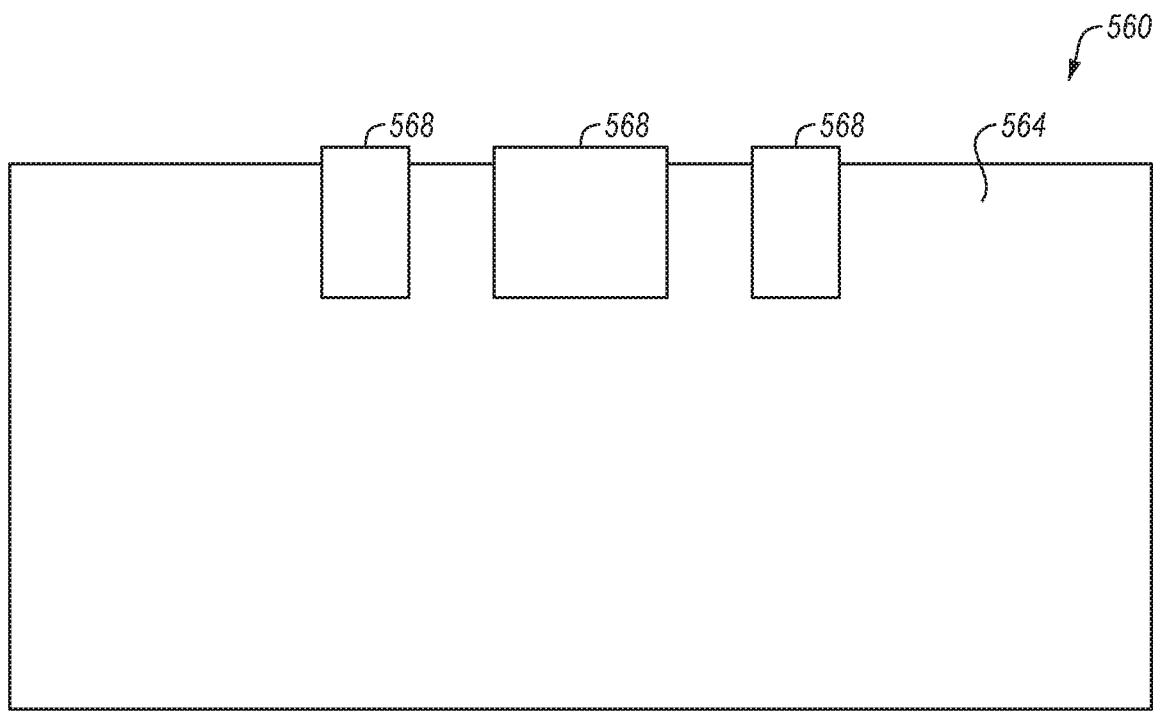
FIGS. 10A-10B illustrate side views of example embodiments of lift electromagnets.
Figure 10B:
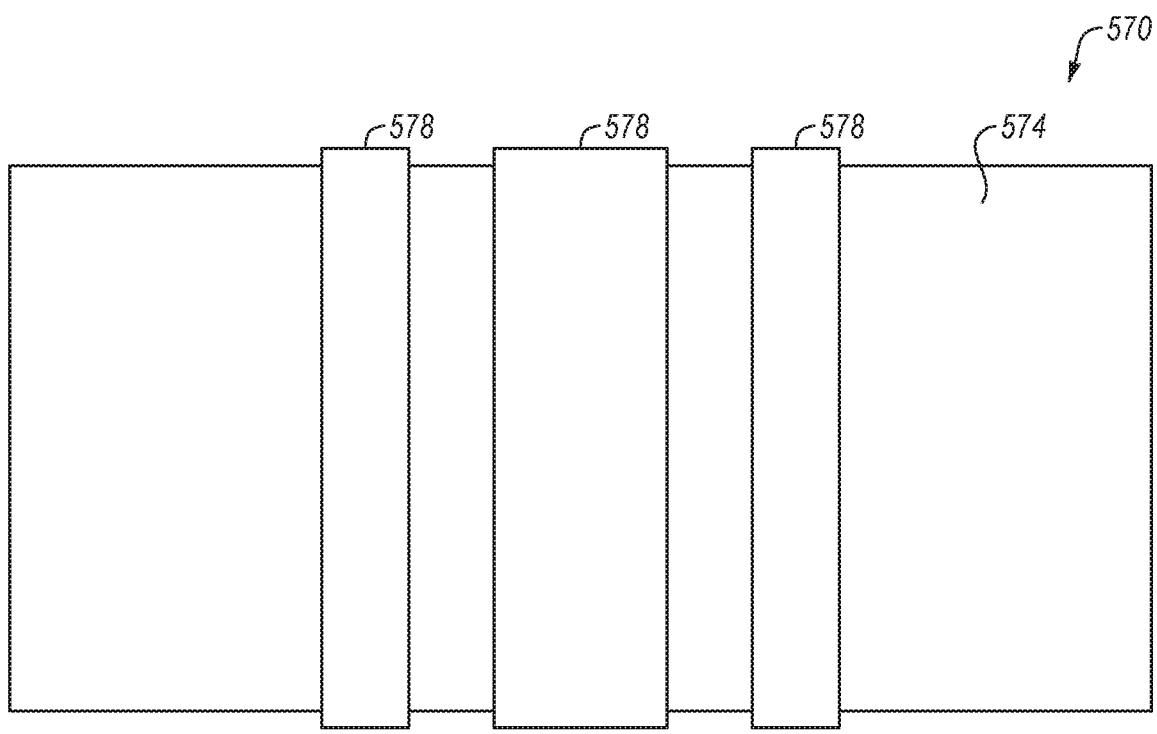

As shown in FIGS. 9A-9B, in some configurations the pole inserts may include a rectangular cross section with a rounded or countered surface. In other configurations, the pole inserts may include annular or ring-shaped configurations. FIGS. 10A-10B illustrate an example of a lift electromagnet with annular or ring-shaped pole inserts.

FIG. 10A illustrates a side view of another example embodiment of a lift electromagnet 560. As illustrated, in some configurations the lift electromagnet 520 may include curved or contoured pole inserts 568 that extends around at least a part of the circumference of an insert wall 564. The pole inserts 568 may extend through the insert wall 564 between an exterior and interior, to be positioned proximate a lift shaft (not shown).

FIG. 10B illustrates a side view of another example embodiment of a lift electromagnet 570. As shown, the lift electromagnet 570 includes annular or ring-shaped pole inserts 578 extending around a circumference of an insert wall 574. The pole inserts 578 may extend through the insert wall 574 between an exterior and interior, to be positioned proximate a lift shaft (not shown). In the illustrated configuration, the pole inserts 578 extend around the entire insert wall 574, forming a concentric ring around the lift shaft. In other configurations, the pole inserts 578 may extend around a portion of the insert wall 574. For example, the pole inserts 578 may extend around half of the circumference of the insert wall 574, forming half rings. In another example, pole inserts may extend around less than half of the circumference of the insert wall, such as the configuration of the pole inserts 568 of FIG. 10A. In other configurations, the pole inserts 578 may be formed to extend around any suitable portion of the circumference of the insert wall 574.

In further configurations, the pole inserts 578 may include rings around the insert wall 574 and/or the lift shaft, but such rings may not be concentric with the insert wall 574 and/or the lift shaft. An example of such a configuration is illustrated in FIG. 5G.

FIGS. 11A-11B illustrate cross section views of another example embodiment of a lift electromagnet 580. As illustrated, the lift electromagnet 580 includes ring-shaped pole inserts 588 extending through and coupled to an insert wall 582. The insert wall 582 may at least partially define a vacuum envelope, and may surround a lift shaft 584 and a rotor 586, which may be part of a motor assembly that rotates an anode. The lift shaft 584 and the rotor 586 may rotate about a centerline 587. However, rather than being positioned concentrically with the centerline 587, the pole inserts 588 extend around a centerline 589 that is offset from the centerline 587. In such configurations, the pole inserts 588 are positioned closer to the lift shaft 584 on one side, and therefore exert a lifting force on the side where the pole inserts 588 are closer to the lift shaft 584.

As shown in FIG. 11B, the lift shaft 584 and the pole inserts 588 may not be concentric with one another. In such configuration, a gap A between the lift shaft 584 and the pole inserts 588 may be greater on one side of the lift shaft 584 than a gap B on the other, opposite side of the lift shaft 584. Thus, gap A can be smaller than gap B.

FIGS. 12A-12E illustrate schematic cross sectional representations of example manufacturing steps for a lift electromagnet in an insert wall. At step 610, a body 612 of the insert wall may be provided. In some configurations, the body 612 may be formed of stainless steel or other suitable materials. The body 612 may be substantially cylindrical. In some configurations, the outer diameter of the body 612 may correspond to a desired outer diameter of an insert wall of a lift electromagnet.

At step 620, the body 612 may be machined to create a recess 622 and openings 624. The size and shape of the openings may correspond to pole inserts that are to be inserted therein. At step 630, pole inserts 632 may be positioned into the openings 624. At step 640, a backfill or braze material 642 may be positioned in the recess 622. The backfill 642 material may retain the pole inserts 632 in the opening. Additionally or alternatively, the backfill 642 material may retain the pole inserts 632 with respect to the body 612. In some configurations, the backfill or braze material 642 may include copper. The backfill or braze material 642 may be melted or heated to increase its viscosity, and may be positioned into the recess 622 until it solidifies, cures or hardens. At step 650, an opening 652 may be machined in the body 612. The opening 652 may be sized and shaped to receive a lift shaft of a lift assembly. In some configurations, the opening 652 may be positioned to receive a lift shaft such that the lift shaft is concentric with other rotating components in an X-ray source.

Figure 13:
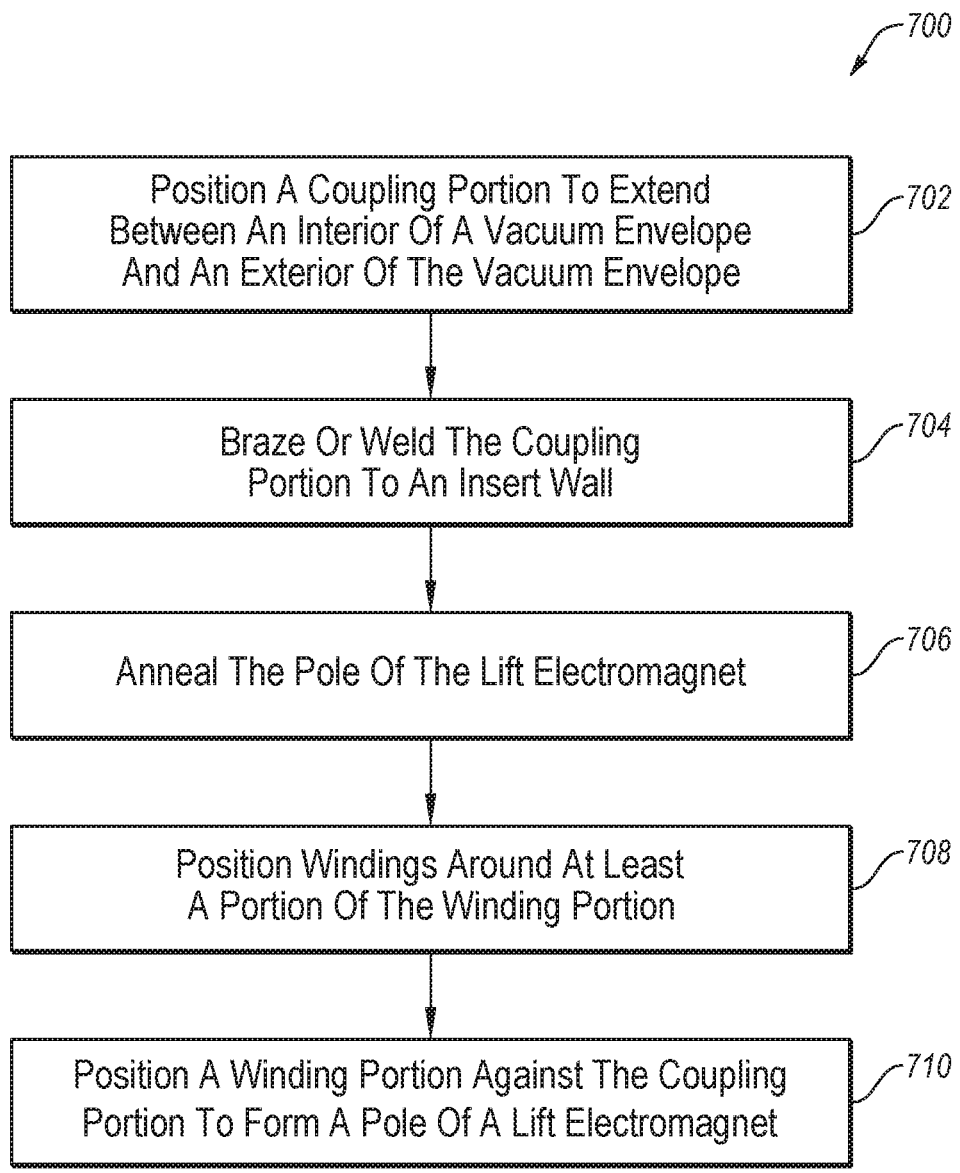
FIG. 13 is a flow chart of an example method for manufacturing a lift electromagnet.

FIG. 13 is a flow chart of an example method 700 for manufacturing a lift electromagnet in an insert wall. At step 702, a coupling may be positioned to extend between an interior of a vacuum envelope an exterior of the vacuum envelope.

In some embodiments, the method 700 may include step 704, where the coupling portion is brazed or welded to an insert wall that at least partially defines the vacuum envelope. In some embodiments, the brazing or welding the coupling portion to the insert wall may hermetically seal the vacuum envelope. In other embodiments, the coupling portion may be coupled to the insert wall in other suitable manners.

At step 706, the pole of the lift electromagnet may be annealed. Annealing may include heat treatment of the pole of the lift electromagnet (e.g., the coupling portion, the winding portion, or both) to alter its magnetic properties. In some embodiments, the pole may be annealed so it has desired magnetic properties, for example, sufficiently high magnetic permeability to apply a magnetic force to a lift shaft coupled to the anode. In annealing, atoms migrate in the crystal lattice, leading to changes in magnetic properties. As the material cools it recrystallizes. In some circumstances, the magnetic properties of a material may depend on temperature, heating rate, cooling rate, and the atmosphere surrounding the material. In such circumstances, the annealing may be controlled by varying those (or other) conditions. For example, annealing to change the magnetic properties may include heating a material over the curie temperature of the material. In some configurations, annealing may include heating the material between 150 Celsius and 900 Celsius, depending on the material used and other conditions. In addition, further heat treatments may be used to achieve desired properties.

At step 708, windings may be positioned around at least a portion of the winding portion. In some aspects, the windings may be positioned around an interface between the winding portion and the coupling portion, although other configurations may be implemented.

At step 710, a winding portion may be positioned against the coupling portion to form at least one pole of a lift electromagnet. The lift electromagnet and/or the pole may be configured to exert a force on the anode.

For the processes and/or methods disclosed, the functions performed in the processes and methods may be implemented in differing order as may be indicated by context. Furthermore, the outlined steps and operations are only provided as examples, and some of the steps and operations may be optional, combined into fewer steps and operations, or expanded into additional steps and operations.

In one example embodiment, a lift assembly (220) may exert a force on a rotatable anode (242) of an X-ray source (210). The lift assembly (220) may include a lift shaft (226) and a lift electromagnet (222). The lift shaft (226) may be coupled to an anode (242) and configured to rotate around an axis of rotation of the anode (242). The lift electromagnet (222) may be configured to apply a magnetic force to the lift shaft (226) in a radial direction. The lift electromagnet (222) may include a coupling portion (363, 365, 367) extending between an interior of a vacuum envelope and an exterior of the vacuum envelope and a winding portion (366, 368, 370) coupled to the coupling portion (363, 365, 367). Windings (391) may at least partially surround the winding portion (366, 368, 370).

In some aspects, at least one dimension of the coupling portion (363, 365, 367) at the interface between the coupling portion (363, 365, 367) and the winding portion (366, 368, 370) may be larger than a corresponding dimension of the winding portion (366, 368, 370). In some embodiments, the windings (391) may extend proximate an interface between the coupling portion (363, 365, 367) and the winding portion (366, 368, 370) or the windings (391) extend to fully cover the interface between the coupling portion (363, 365, 367) and the winding portion (366, 368, 370).

The lift assembly (220) may include an alignment feature configured to align the coupling portion (363, 365, 367) with respect to the insert wall (382). The alignment feature may include a flange defined in the coupling portion (363, 365, 367) that retains the coupling portion (363, 365, 367) when it is positioned inside of an opening defined by the insert wall (382). Additionally or alternatively, the alignment feature may include a taper extending between a lower portion and an upper portion of the coupling portion (363, 365, 367). The taper may retain the coupling portion (363, 365, 367) when it is positioned inside of an opening defined by the insert wall (382). The coupling portion (363, 365, 367) may define an opening sized and shaped to receive the winding portion (366, 368, 370).

The lift electromagnet (222) may include at least three poles oriented towards the lift shaft (226). The coupling portion (363, 365, 367), the winding portion (366, 368, 370) and the windings (391) may be part of at least one of the three poles. The lift electromagnet (222) may include a wall insert coupled to the insert wall (382), and at least three poles oriented towards the lift shaft (226) extending through the wall insert.

In some embodiments, the interface between the coupling portion (363, 365, 367) and the winding portion (366, 368, 370) may be substantially planar. The lift assembly (220) may be operably coupled to an anode assembly (240) that includes an insert wall (382) defining the vacuum envelope. The anode (242) may be positioned inside the vacuum envelope and may be spaced apart from a cathode configured to generate electrons.

The winding portion (366, 368, 370) may be positioned on the exterior of the vacuum envelope and the coupling portion (363, 365, 367) extends through an insert wall (382) defining the vacuum envelope. A braze or a weld may be positioned between the insert wall (382) and the coupling portion (363, 365, 367). The coupling portion (363, 365, 367) and/or the wilding portion may include low carbon steel, high purity iron, cobalt-iron, or nickel-iron. Additionally or alternatively, the winding portion (366, 368, 370) may include stainless steel or ceramic.

In another example embodiment, a lift assembly (220) may be configured to exert a force on a rotatable anode (242) of the anode assembly (240). The lift assembly (220) may include a lift shaft (226) coupled to an anode (242) and configured to rotate around an axis of rotation of the anode (242) and a lift electromagnet (222) that includes means for coupling at least one pole to an insert wall (382) that at least partially defines a vacuum envelope such that the pole extends between an interior of the vacuum envelope and an exterior of the vacuum envelope.

The terms and words used in this description and claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

Aspects of the present disclosure may be embodied in other forms without departing from its spirit or essential characteristics. The described aspects are to be considered in all respects illustrative and not restrictive. The claimed subject matter is indicated by the appended claims rather than by the foregoing description. All changes which come within the meaning and range of equivalency of the claims are to be embraced within their scope.

What is claimed is:

1. A lift assembly configured to exert a force on a rotatable anode of an X-ray source, the lift assembly comprising:
   a lift shaft coupled to an anode and configured to rotate around an axis of rotation of the anode; and
   a lift electromagnet configured to apply a magnetic force to the lift shaft in a radial direction, the lift electromagnet comprising:
      a coupling portion extending between an interior of a vacuum envelope and an exterior of the vacuum envelope;
      a winding portion coupled to the coupling portion; and
      windings at least partially surrounding the winding portion.

2. The lift assembly of claim 1, wherein at least one dimension of the coupling portion at the interface between the coupling portion and the winding portion is larger than a corresponding dimension of the winding portion.

3. The lift assembly of claim 1, wherein the windings extend proximate an interface between the coupling portion and the winding portion or the windings extend to fully cover the interface between the coupling portion and the winding portion.

4. The lift assembly of claim 1, further comprising an alignment feature configured to align the coupling portion with respect to the insert wall.

5. The lift assembly of claim 4, the alignment feature comprising a flange defined in the coupling portion that retains the coupling portion when it is positioned inside of an opening defined by the insert wall.

6. The lift assembly of claim 4, the alignment feature comprising a taper extending between a lower portion and an upper portion of the coupling portion, wherein the taper retains the coupling portion when it is positioned inside of an opening defined by the insert wall.

7. The lift assembly of claim 1, wherein the coupling portion defines an opening sized and shaped to receive the winding portion.

8. The lift assembly of claim 1, the lift electromagnet comprising at least three poles oriented towards the lift shaft, wherein the coupling portion, the winding portion and the windings are part of at least one of the three poles.

9. The lift assembly of claim 1, the lift electromagnet comprising a wall insert coupled to the insert wall, and at least three poles oriented towards the lift shaft extending through the wall insert.

10. The lift assembly of claim 1, wherein the interface between the coupling portion and the winding portion is substantially planar.

11. The lift assembly of claim 1, operably coupled to an anode assembly comprising an insert wall defining the vacuum envelope, wherein the anode is positioned inside the vacuum envelope and is spaced apart from a cathode configured to generate electrons.

12. The lift assembly of claim 1, wherein the winding portion is positioned on the exterior of the vacuum envelope and the coupling portion extends through an insert wall defining the vacuum envelope.

13. The lift assembly of claim 12, further comprising a braze or a weld between the insert wall and the coupling portion.

14. The lift assembly of claim 12, wherein:
   the coupling portion or the wilding portion comprises low carbon steel, high purity iron, cobalt-iron, or nickel-iron; or
   the winding portion comprises stainless steel or ceramic.

15. A method of manufacturing a lift assembly configured to exert a force on a rotatable anode of an X-ray source, the method comprising:
   positioning a coupling portion to extend between an interior of a vacuum envelope an exterior of the vacuum envelope; and
   positioning a winding portion against the coupling portion to form at least one pole of a lift electromagnet, the lift electromagnet configured to exert a force on the anode.

16. The method of claim 15, further comprising brazing or welding the coupling portion to an insert wall that at least partially defines the vacuum envelope.

17. The method of claim 15, further comprising annealing the pole of the lift electromagnet.

18. The method of claim 15, further comprising positioning windings around at least a portion of the winding portion.

19. The method of claim 15, further comprising positioning windings around an interface between the winding portion and the coupling portion.

20. A lift assembly configured to exert a force on a rotatable anode of the anode assembly, comprising:
   a lifting shaft means coupled to an anode and configured to rotate around an axis of rotation of the anode;
   a lift electromagnetic means for apply a magnetic force to the lift shaft in a radial direction;

a coupling means for extending between an interior of a vacuum envelope and an exterior of the vacuum envelope;
a winding means for coupling to the coupling means and receiving windings at least partially surrounding the winding means.

\* \* \* \* \*